United States Patent
Kroger Lyons et al.

(10) Patent No.: US 11,865,198 B2
(45) Date of Patent: Jan. 9, 2024

(54) TRANSPARENT COMPOSITION WITH SOLUBLE SCALP HEALTH ACTIVE

(71) Applicant: The Procter & Gamble Company, Cincinnati, OH (US)

(72) Inventors: Kelly Rose Kroger Lyons, Liberty Township, OH (US); Eric Scott Johnson, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/126,369

(22) Filed: Dec. 18, 2020

(65) Prior Publication Data

US 2021/0186839 A1 Jun. 24, 2021

Related U.S. Application Data

(60) Provisional application No. 62/950,579, filed on Dec. 19, 2019.

(51) Int. Cl.

| | |
|---|---|
| *A61K 8/49* | (2006.01) |
| *A61K 8/46* | (2006.01) |
| *A61K 8/02* | (2006.01) |
| *A61Q 5/12* | (2006.01) |
| *A61K 8/19* | (2006.01) |
| *A61K 8/34* | (2006.01) |
| *A61K 8/365* | (2006.01) |
| *A61K 8/368* | (2006.01) |
| *A61K 8/37* | (2006.01) |
| *A61K 8/41* | (2006.01) |
| *A61K 8/44* | (2006.01) |
| *A61K 8/73* | (2006.01) |
| *A61K 8/81* | (2006.01) |
| *A61K 8/89* | (2006.01) |
| *A61Q 5/00* | (2006.01) |

(52) U.S. Cl.
CPC .......... *A61K 8/4953* (2013.01); *A61K 8/0241* (2013.01); *A61K 8/19* (2013.01); *A61K 8/34* (2013.01); *A61K 8/365* (2013.01); *A61K 8/368* (2013.01); *A61K 8/37* (2013.01); *A61K 8/416* (2013.01); *A61K 8/44* (2013.01); *A61K 8/463* (2013.01); *A61K 8/466* (2013.01); *A61K 8/49* (2013.01); *A61K 8/4926* (2013.01); *A61K 8/4946* (2013.01); *A61K 8/73* (2013.01); *A61K 8/737* (2013.01); *A61K 8/8147* (2013.01); *A61K 8/89* (2013.01); *A61Q 5/006* (2013.01); *A61Q 5/12* (2013.01); *A61K 2800/262* (2013.01); *A61K 2800/48* (2013.01); *A61K 2800/546* (2013.01); *A61K 2800/548* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | | | |
|---|---|---|---|---|
| 6,113,931 | A | * | 9/2000 | Bonda ..................... A61Q 17/04 424/59 |
| 6,147,038 | A | * | 11/2000 | Halloran ................. A61K 8/898 510/423 |
| 9,610,234 | B2 | | 4/2017 | Mann et al. |
| 9,890,107 | B2 | | 2/2018 | Schuch et al. |
| 10,391,046 | B2 | | 8/2019 | Hartnett et al. |
| 2002/0165283 | A1 | | 11/2002 | Lutz |
| 2004/0234484 | A1 | | 11/2004 | Peffly |
| 2006/0171911 | A1 | | 8/2006 | Schwartz et al. |
| 2007/0020220 | A1 | | 1/2007 | Osborne |
| 2007/0202069 | A1 | | 8/2007 | Tamareselvy |
| 2008/0145328 | A1 | | 6/2008 | Schwartz et al. |
| 2008/0206179 | A1 | | 8/2008 | Peffly |
| 2009/0169644 | A1 | | 7/2009 | Goddinger et al. |
| 2015/0297489 | A1 | | 10/2015 | Kleinen et al. |
| 2015/0328135 | A1 | | 11/2015 | Argembeaux et al. |
| 2016/0015615 | A1 | | 1/2016 | Mann et al. |
| 2017/0000710 | A1 | | 1/2017 | Klug et al. |

(Continued)

FOREIGN PATENT DOCUMENTS

| | | |
|---|---|---|
| EP | 2786742 A1 | 10/2014 |
| JP | S61238716 A | 10/1986 |

(Continued)

OTHER PUBLICATIONS

PCT Search Report and Written Opinion for PCT/US2020/065817 dated May 11, 2021.

(Continued)

*Primary Examiner* — Jennifer A Berrios
(74) *Attorney, Agent, or Firm* — Linda M. Sivik

(57) ABSTRACT

The present invention is directed to a personal care composition comprising from about 12% to about 25% of one or more surfactants; from about 0.01% to 10% of one or more soluble scalp health active; from about 0.1% to about 4% of a thickening polymer wherein the thickening polymer is selected from the group consisting of homopolymers based on acrylic acid, methacrylic acid or other related derivatives, alkali swellable and hydrophobically-modified alkali swellable acrylic copolymers or methacrylate copolymers, soluble crosslinked acrylic polymers, associative polymeric thickeners and mixtures thereof; from 0.01% to 0.8% of a cationic polymer; wherein the personal care composition has a pH of about 4.5 to about 6 and wherein the personal care composition has a Haze value less than or equal to 25.

16 Claims, 12 Drawing Sheets

(56) References Cited

U.S. PATENT DOCUMENTS

| | | |
|---|---|---|
| 2017/0239155 A1 | 8/2017 | Hartnett |
| 2017/0333320 A1 | 11/2017 | Carnali et al. |
| 2018/0311135 A1* | 11/2018 | Chang .................... A61K 8/817 |
| 2019/0105247 A1 | 4/2019 | Song et al. |
| 2019/0167554 A1 | 6/2019 | Wankhade |
| 2019/0328647 A1 | 10/2019 | Chang et al. |
| 2021/0121378 A1 | 4/2021 | Chang et al. |
| 2021/0121381 A1 | 4/2021 | Chang et al. |
| 2021/0121382 A1 | 4/2021 | Chang et al. |

FOREIGN PATENT DOCUMENTS

| | | |
|---|---|---|
| JP | H08310925 A | 11/1996 |
| JP | 2007153791 A | 6/2007 |
| JP | 2016030722 A | 3/2016 |
| WO | 2012017091 A2 | 2/2012 |
| WO | 2012052536 A2 | 4/2012 |

OTHER PUBLICATIONS

All Office Actions, U.S. Appl. No. 17/078,781.
All Office Actions, U.S. Appl. No. 17/078,796.
All Office Actions, U.S. Appl. No. 17/078,813.
All Office Actions; U.S. Appl. No. 17/980,169, filed Nov. 3, 2022.
All Office Actions; U.S. Appl. No. 17/980,199, filed Nov. 3, 2022.
Document D5, OECD Guideline for Testing of Chemicals, Ready Biodegradability, vol. 301, Jul. 17, 1992, 62 pages.
Document D6, Ok Compost and Seedling, 3 pages. (No date available).
Unpublished U.S. Appl. No. 17/980,169, filed Nov. 3, 2022 to Debora W. Chang et al.
Unpublished U.S. Appl. No. 17/980,199, filed Nov. 3, 2022 to Debora W. Chang et al.

* cited by examiner

TRANSPARENT COMPOSITION WITH SOLUBLE SCALP HEALTH ACTIVE

FIELD OF THE INVENTION

The present invention is directed to a personal care composition comprising a surfactant, thickening polymer and cationic polymer achieving a transparent appearance and low haze value.

BACKGROUND OF THE INVENTION

For years, anti-dandruff shampoos have been widely used to treat dandruff and clean hair and scalp, but most of them appear opaque or pearlescent. The anti-dandruff agents can be soluble substances such as climbazole, piroctone olamine, or azoxystrobin, and referred to as soluble scalp health actives. In general, anti-dandruff shampoos are formulated with soluble scalp health actives in combination with surfactants and aqueous systems that are intended to deposit the soluble scalp health actives on the scalp. These systems can contain an anionic thickening polymer to help thicken the low viscosity solution; as well as, a cationic polymer to help improve the usage experience. The combination of certain anionic thickening polymers and cationic polymers in the system typically leads to products that are not clear. As consumers' desire for a clear anti-dandruff shampoo that delivers superior anti-dandruff efficacy is increasing, there remains a need for a shampoo containing surfactant and both anionic thickening polymer and cationic polymer that appears clear.

It has been surprisingly found that the addition of specific thickening polymers to a shampoo composition containing select surfactant levels, surfactant types, and select cationic polymers will appear clear in the bottle and in hand. In the past similar cationic polymers added to a similar solution with a specific anionic polymer would yield a hazy, unclear composition. It has been shown in the present invention that compositions can generate clear formulas when the ratio of anionic thickening polymer, cationic polymer type, surfactant level, and pH are ideal.

SUMMARY OF THE INVENTION

The present invention is directed to a personal care composition comprising from about 12% to about 25% of one or more surfactants; from about 0.01% to 10% of one or more soluble scalp health active; from about 0.1% to about 4% of a thickening polymer wherein the thickening polymer is selected from the group consisting of homopolymers based on acrylic acid, methacrylic acid or other related derivatives, alkali swellable and hydrophobically-modified alkali swellable acrylic copolymers or methacrylate copolymers, soluble crosslinked acrylic polymers, associative polymeric thickeners and mixtures thereof; from 0.01% to 0.8% of a cationic polymer; wherein the personal care composition has a pH of about 4.5 to about 6 and wherein the personal care composition has a Haze value less than or equal to 25.

DETAILED DESCRIPTION OF EMBODIMENTS OF THE INVENTION

Figure 1:
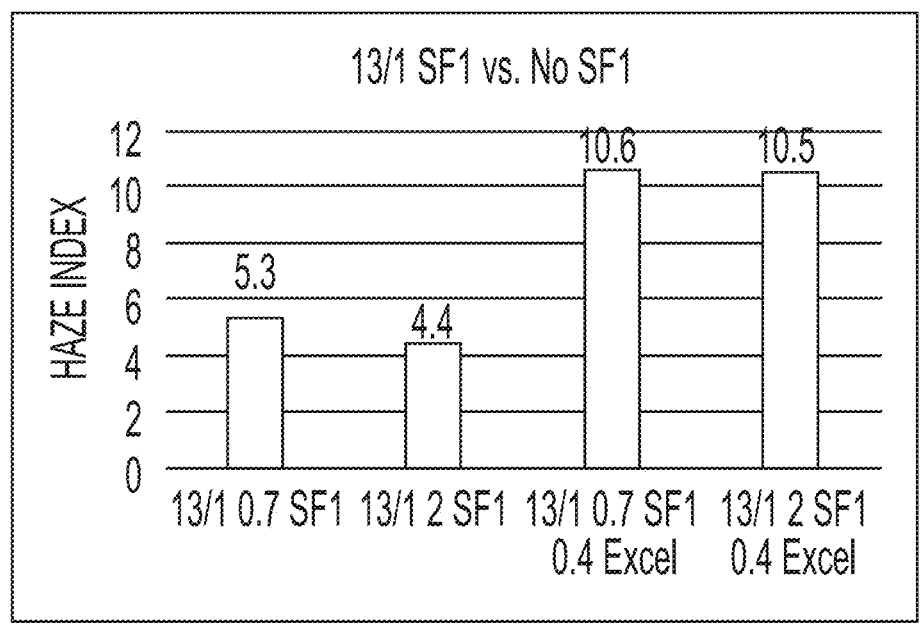
FIG. 1 is a graph showing anionic polymer Carbopol Aqua SF1 (with 13% Sodium Laureth-1 Sulfate (SLE1S) surfactant and 1% Sodium Deceth-1 Sulfate (C10E1) surfactant)) vs. No Carbopol Aqua SF1.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

While the specification concludes with claims particularly pointing out and distinctly claiming the invention, it is believed that the present invention will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the personal care composition.

As used herein, "personal care compositions" includes products such as shampoos, shower gels, liquid hand cleansers, hair colorants, facial cleansers, and other surfactant-based liquid compositions As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Soluble Scalp Health Active

Soluble scalp health active may be one material or a mixture selected from the groups consisting of: azoles, such as climbazole, ketoconazole, itraconazole, econazole, and elubiol; hydroxy pyridones, such as piroctone olamine, ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline, and hinokitol.

The azole soluble scalp health active may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole soluble scalp health active may be ketoconazole. The sole soluble scalp health active may be ketoconazole.

The soluble scalp health active may be present in an amount from about 0.01% to 10%, from about 0.1% to about 9%, from about 0.25% to 8%, from about 0.5% to 6%, and from about 0.5% to 3%. The soluble scalp health active can be surfactant soluble and thus surfactant soluble scalp health active.

A. Detersive Surfactant

The personal care composition may comprise greater than about 10% by weight of a surfactant system which provides cleaning performance to the composition, and may be greater than 12% by weight of a surfactant system which provides cleaning performance to the composition. The surfactant system comprises an anionic surfactant and/or a combination of anionic surfactants and/or a combination of anionic surfactants and co-surfactants selected from the group consisting of amphoteric, zwitterionic, nonionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The personal care composition may comprise from about 12% to about 25%, from about 12% to about 20%; from about 12% to about 18%; from about 12% to about 14%, by weight of one or more surfactants.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the personal care composition include ammonium lauryl sulfate, ammonium laureth sulfate, ammonium C10-15 pareth sulfate, ammonium C10-15 alkyl sulfate, ammonium C11-15 alkyl sulfate, ammonium decyl sulfate, ammonium deceth sulfate, ammonium undecyl sulfate, ammonium undeceth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, sodium C10-15 pareth sulfate, sodium C10-15 alkyl sulfate, sodium C11-15 alkyl sulfate, sodium decyl sulfate, sodium deceth sulfate, sodium undecyl sulfate, sodium undeceth sulfate, potassium lauryl sulfate, potassium laureth sulfate, potassium C10-15 pareth sulfate, potassium C10-15 alkyl sulfate, potassium C11-15 alkyl sulfate, potassium decyl sulfate, potassium deceth sulfate, potassium undecyl sulfate, potassium undeceth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, TEA-dodecyl benzene sulfonate, sodium cocoyl isethionate, sodium cocoyl methyl isethionate, sodium methyl cocoyl taurate, sodium methyl lauroyl taurate, sodium caproyl methyltaurate, sodium cocoyl glutamate, disodium cocoyl glutamate, disodium capryloyl glutamate, sodium lauryl sulfoacetate, sodium methyl 2-sulfolaurate, disodium 2-sulfolaurate, sodium cocoyl glycinate, sodium lauroyl glycinate, and combinations thereof. The anionic surfactant may be sodium lauryl sulfate or sodium laureth sulfate.

The composition of the present invention can also include anionic surfactants selected from the group consisting of:
a) $R_1 O(CH_2CHR_3O)_y SO_3M$;
b) $CH_3 (CH_2)_z CHR_2 CH_2 O(CH_2 CHR_3O)_y SO_3M$; and
c) mixtures thereof,
where $R_1$ represents $CH_3 (CH_2)_{10}$, $R_2$ represents H or a hydrocarbon radical comprising 1 to 4 carbon atoms such that the sum of the carbon atoms in z and $R_2$ is 8, $R_3$ is H or $CH_3$, y is 0 to 7, the average value of y is about 1 when y is not zero (0), and M is a monovalent or divalent, positively-charged cation.

Suitable anionic alkyl sulfates and alkyl ether sulfate surfactants include, but are not limited to, those having branched alkyl chains which are synthesized from C8 to C18 branched alcohols which may be selected from the group consisting of: Guerbet alcohols, aldol condensation derived alcohols, oxo alcohols, F-T oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfate and sodium trideceth-3 sulfate. The composition of the present invention can also include sodium tridecyl sulfate.

The composition of the present invention can also include anionic alkyl and alkyl ether sulfosuccinates and/or dialkyl and dialkyl ether sulfosuccinates and mixtures thereof. The dialkyl and dialkyl ether sulfosuccinates may be a C6-15 linear or branched dialkyl or dialkyl ether sulfosuccinate. The alkyl moieties may be symmetrical (i.e., the same alkyl moieties) or asymmetrical (i.e., different alkyl moieties). Nonlimiting examples include: disodium lauryl sulfosuccinate, disodium laureth sulfosuccinate, sodium bistridecyl sulfosuccinate, sodium dioctyl sulfosuccinate, sodium dihexyl sulfosuccinate, sodium dicyclohexyl sulfosuccinate, sodium diamyl sulfosuccinate, sodium diisobutyl sulfosuccinate, linear bis(tridecyl) sulfosuccinate and mixtures thereof.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

"Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

The personal care composition may comprise a co-surfactant. The co-surfactant can be selected from the group consisting of amphoteric surfactant, zwitterionic surfactant, non-ionic surfactant and mixtures thereof. The co-surfactant can include, but is not limited to, lauramidopropyl betaine, cocoamidopropyl betaine, lauryl hydroxysultaine, sodium lauroamphoacetate, disodium cocoamphodiacetate, cocamide monoethanolamide and mixtures thereof.

The personal care composition may further comprise from about 0.25% to about 15%, from about 1% to about 14%, from about 2% to about 13% by weight of one or more amphoteric, zwitterionic, nonionic co-surfactants, or a mixture thereof.

Suitable amphoteric or zwitterionic surfactants for use in the personal care composition herein include those which are known for use in personal care compositions such as shampoo or other personal care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphodiacetate, sodium cocoamphohydroxypropylsulfonate, sodium cocoamphopropionate, sodium cornamphopropionate, sodium lauraminopropionate, sodium lauroamphoacetate, sodium lauroamphodiacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphodiacetate, ammonium cocoamphohydroxypropylsulfonate, ammonium cocoamphopropionate, ammonium cornamphopropionate, ammonium lauraminopropionate, ammonium lauroamphoacetate, ammonium lauroamphodiacetate, ammonium lauroamphohydroxypropylsulfonate, ammonium lauroamphopropionate, ammonium cornamphopropionate, ammonium lauriminodipropionate, triethanolamine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminopropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The composition may comprises a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof.

Suitable nonionic surfactants for use in the present invention include those described in McCutcheion's Detergents and Emulsifiers, North American edition (1986), Allured Publishing Corp., and McCutcheion's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

The co-surfactant can be a non-ionic surfactant selected from the alkanolamides group including: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, PPG-2 Hydroxyethyl Isostearamide and mixtures thereof.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Texas under the trade names Neodol® 91, Neodol® 23, Neodol® 25, Neodol® 45, Neodol® 135, Neodol® 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Delaware, including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula $(S)_n$-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tx.

Other nonionic surfactants suitable for use in the present invention are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tx.) and octylphenol ethoxylates (Triton™ X-15, X-35, X-45, X-114, X-100, X-102, X-165, X-305, X-405, X-705 available from The Dow Chemical Company, Houston, TX).

Also suitable for use herein are tertiary alkylamine oxides including lauramine oxide and cocamine oxide.

Non limiting examples of other anionic, zwitterionic, amphoteric, and non-ionic additional surfactants suitable for use in the personal care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Suitable surfactant combinations comprise an average weight % of alkyl branching of from about 0.5% to about 30%, alternatively from about 1% to about 25%, alternatively from about 2% to about 20%. The surfactant combination can have a cumulative average weight % of C8 to C12 alkyl chain lengths of from about 7.5% to about 25%, alternatively from about 10% to about 22.5%, alternatively from about 10% to about 20%. The surfactant combination can have an average C8-C12/C13-C18 alkyl chain ratio from about 3 to about 200, alternatively from about 25 to about 175.5, alternatively from about 50 to about 150, alternatively from about 75 to about 125.

B. Cationic Polymers

The personal care composition also comprises a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The personal care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer may be, including but not limited to a cationic guar polymer, has a weight average Molecular weight of less than 2.2 million g/mol, or from about 150 thousand to about 2.2 million g/mol, or from about 200 thousand to about 2.2 million g/mol, or from about 300 thousand to about 1.2 million g/mol, or from about 750,000 thousand to about 1 million g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.8 meq/g.

The cationic guar polymer may have a weight average Molecular weight of less than about 1.5 million g/mol, and has a charge density of from about 0.1 meq/g to about 2.5 meq/g. The cationic guar polymer may have a weight average molecular weight of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol or from about 150 thousand to about 800 thousand g/mol, or from about 200 thousand to about 700 thousand g/mol, or from about 300 thousand to about 700 thousand g/mol, or from about 400 thousand to about 600 thousand g/mol. The cationic guar polymer may have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The cationic guar polymer may be formed from quaternary ammonium compounds. The quaternary ammonium compounds for forming the cationic guar polymer may conform to the general formula 1:

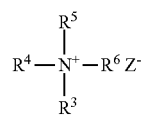

wherein where $R^3$, $R^4$ and $R^5$ are methyl or ethyl groups; $R^6$ is either an epoxyalkyl group of the general formula 2:

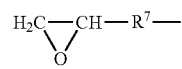

or $R^6$ is a halohydrin group of the general formula 3:

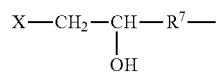

wherein $R^7$ is a $C_1$ to $C_3$ alkylene; X is chlorine or bromine, and Z is an anion such as Cl−, Br−, I− or $HSO_4$−.

The cationic guar polymer may conform to the general formula 4:

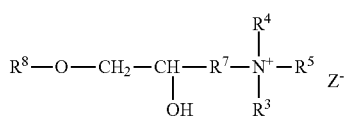

wherein $R^8$ is guar gum; and wherein $R^4$, $R^5$, $R^6$ and $R^7$ are as defined above; and wherein Z is a halogen. The cationic guar polymer may conform to Formula 5:

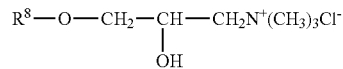

Suitable cationic guar polymers include cationic guar gum derivatives, such as guar hydroxypropyltrimonium chloride. The cationic guar polymer may be a guar hydroxypropyltrimonium chloride. Specific examples of guar hydroxypropyltrimonium chlorides include the Jaguar® series commercially available from Solvay, for example Jaguar® C-500, commercially available from Solvay. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.3 meq/g and a molecular weight of about 500,000 g/mol and is available from Solvay as Jaguar® Optima. Other suitable guar hydroxypropyltrimonium chloride are: guar hydroxypropyltrimonium chloride which has a charge density of about 0.7 meq/g and a molecular weight of about 1,500,000 g/mol and is available from Solvay as Jaguar® Excel. Other suitable guar hydroxypropyltrimonium chloride are: guar hydroxypropyltrimonium chloride which has a charge density of about 1.1 meq/g and a molecular weight of about 500,000 g/mol and is available from ASI, a charge density of about 1.5 meq/g and a molecular weight of about 500,000 g/mole is available from ASI.

Other suitable guar hydroxypropyltrimonium chloride are: Hi-Care 1000, which has a charge density of about 0.7 meq/g and a Molecular weight of about 600,000 g/mole and is available from Solvay; N-Hance 3269 and N-Hance 3270, which have a charge density of about 0.7 meq/g and a molecular weight of about 425,000 g/mol and are available from ASI; N-Hance 3196, which has a charge density of about 0.8 meq/g and a molecular weight of about 1,100,000 g/mol and is available from ASI. AquaCat CG518 has a charge density of about 0.9 meq/g and a Molecular weight of about 50,000 g/mol and is available from ASI. BF-13, which is a borate (boron) free guar of charge density of about 1 meq/g and molecular weight of about 800,000 and BF-17, which is a borate (boron) free guar of charge density of about 1.5 meq/g and molecular weight of about 800,000, and both are available from ASI.

The personal care compositions of the present invention may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β(1-4) glycosidic linkages. The galactose branching arises by way of an α(1-6) linkage. The ratio of mannose monomers to galactose monomers varies according to the species of the plant and also is affected by climate. Non Guar Galactomannan polymer derivatives of the present invention have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

The non-guar galactomannan polymer derivatives may have a M. Wt. from about 1,000 to about 10,000,000, and/or from about 5,000 to about 3,000,000.

The personal care compositions of the invention can also include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

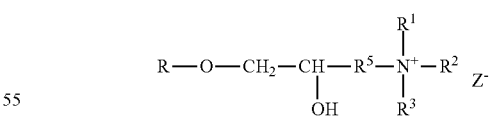

wherein R is the gum. The cationic galactomannan derivative can be a gum hydroxypropyltrimethylammonium chloride, which can be more specifically represented by the general formula 7:

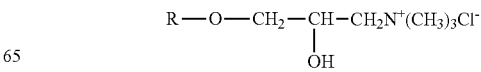

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 1,000 g/mol to about 10,000,000 g/mol, and/or from about 50,000 g/mol to about 1,000,000 g/mol, and/or from about 100,000 g/mol to about 900,000 g/mol, and/or from about 150,000 g/mol to about 400,000 g/mol and a cationic charge density from about 1 meq/g to about 5 meq/g, and/or from 2 meq/g to about 4 meq/g and can be derived from a cassia plant.

The personal care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cationically modified starch polymers disclosed herein have a percent of bound nitrogen of from about 0.5% to about 4%.

The cationically modified starch polymers for use in the personal care compositions can have a molecular weight about 850,000 g/mol to about 1,500,000 g/mol and/or from about 900,000 g/mol to about 1,500,000 g/mol.

The personal care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance of about 80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in personal care compositions are available from known starch suppliers. Also suitable for use in personal care compositions are nonionic modified starch that can be further derivatized to a cationically modified starch as is known in the art. Other suitable modified starch starting materials may be quaternized, as is known in the art, to produce the cationically modified starch polymer suitable for use in personal care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The personal care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

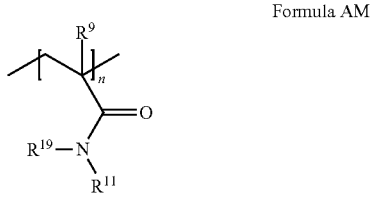

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

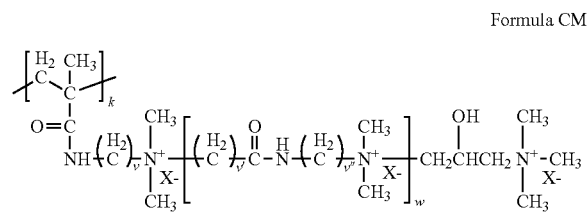

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

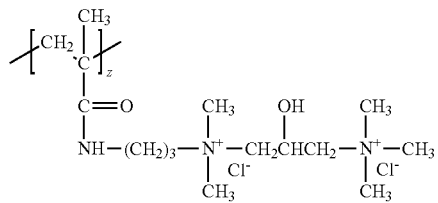

The above structure may be referred to as diquat. Alternatively, the cationic monomer can conform to Formula CM and wherein v and v" are each 3, v'=1, w=1, y=1 and $X^-$ is $Cl^-$, such as:

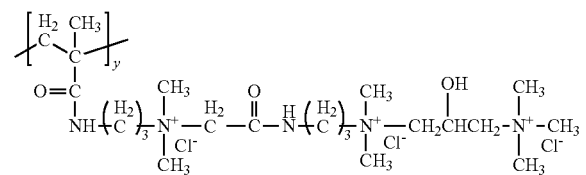

The above structure may be referred to as triquat.

Suitable acrylamide monomer include, but are not limited to, either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl) amino] propyl]ammonio]acetyl]amino]ethyl]2-hydroxy-N,N,N',N',N'-pentamethyl-, trichloride. AM:TRIQUAT is also known as polyquaternium-76 (PQ76). AM:TRIQUAT may have a charge density of 1.6 meq/g and a molecular weight of 1.1 million g/mol.

The cationic copolymer may be of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth) acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth) acrylic acid containing a quaternized N atom may be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth) acrylate; and diethylaminopropyl (meth)acrylate quaternized with methyl chloride. The cationized esters of the (meth)acrylic acid containing a quaternized N atom may be dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 100 thousand g/mol to about 1.5 million g/mol, or from about 300 thousand g/mol to about 1.5 million g/mol, or from about 500 thousand g/mol to about 1.5 million g/mol, or from about 700 thousand g/mol to about 1.0 million g/mol, or from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC may have a charge density of about 1.3 meq/g and a molecular weight of about 1.1 million g/mol. The cationic copolymer can be AM:ATPAC. AM:ATPAC can have a charge density of about 1.8 meq/g and a molecular weight of about 1.1 million g/mol.

(a) Cationic Synthetic Polymers

The personal care composition can comprise a cationic synthetic polymer that may be formed from
i) one or more cationic monomer units, and optionally
ii) one or more monomer units bearing a negative charge, and/or
iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

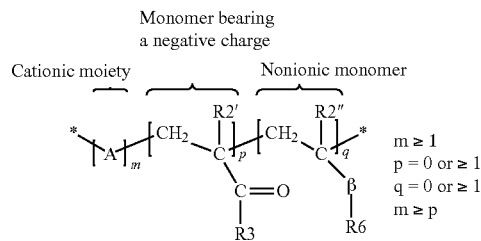

where A, may be one or more of the following cationic moieties:

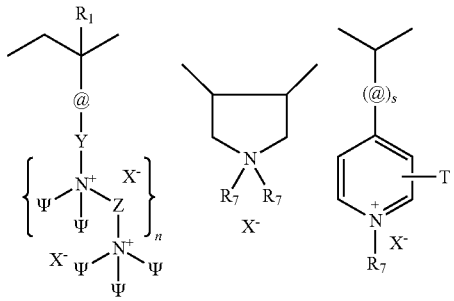

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or ≥1;
where T and R7=C1-C22 alkyl; and
where X−=halogen, hydroxide, alkoxide, sulfate or alkylsulfate.

Where the monomer bearing a negative charge is defined by R2'=H, C1-C4 linear or branched alkyl and R3 as:

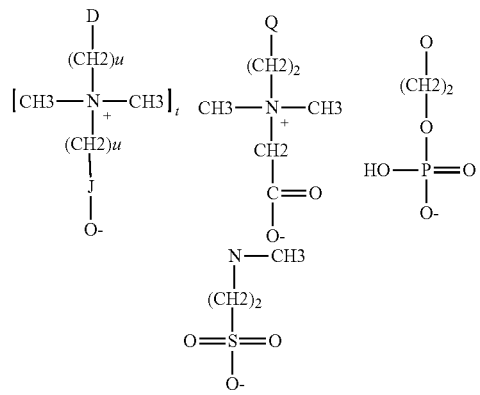

where D=O, N, or S;
where Q=$NH_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

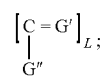

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth) acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth) acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X−) in association with the synthetic cationic polymers may be any known counterion so long as the polymers remain soluble or dispersible in water, in the personal care composition, or in a coacervate phase of the personal care composition, and so long as the counterions are physically and chemically compatible with the essential components of the personal care composition or do not otherwise unduly impair product performance, stability or aesthetics. Non limiting examples of such counterions include halides (e.g., chlorine, fluorine, bromine, iodine), sulfate and methylsulfate.

The cationic polymer described herein can aid in providing damaged hair, particularly chemically treated hair, with a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer returns the hair to a generally virgin-like, healthier state. Lyotropic liquid crystals are formed by combining the synthetic cationic polymers described herein with the aforementioned anionic detersive surfactant component of the personal care composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al. The synthetic polymers described herein can be formulated in a stable personal care composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density may be about 6.2 meq/gm. The polymers also have a M. Wt. of from about 1,000 to about 5,000,000, and/or from about 10,000 to about 1,500,000, and/or from about 100,000 to about 1,500,000.

In the invention cationic synthetic polymers that provide enhanced conditioning and deposition of benefit agents but do not necessarily form lyotropic liquid crystals may have a cationic charge density of from about 0.7 meq/gm to about 7 meq/gm, and/or from about 0.8 meq/gm to about 5 meq/gm, and/or from about 1.0 meq/gm to about 3 meq/gm. The polymers may also have a M. Wt. of from about 1,000 to about 1,500,000, from about 10,000 to about 1,500,000, and from about 100,000 to about 1,500,000.

Suitable cationic cellulose polymers are salts of hydroxyethyl cellulose reacted with trimethyl ammonium substituted epoxide, referred to in the industry (CTFA) as Polyquaternium-10 and available from Dow/Amerchol Corp. (Edison, N.J., USA) in their Polymer LR, JR, and KG series of polymers. Non-limiting examples include: JR-30M, JR-400, KG-30M, JP, LR-30M, LR-400 and mixtures thereof. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium-24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium-67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

The concentration of the cationic polymers ranges about 0.025% to about 5%, from about 0.1% to about 3%, and/or from about 0.2% to about 1%, by weight of the personal care composition.

Thickening Polymers

The personal care composition can comprise a thickening polymer to increase the viscosity of the composition. Suitable thickening polymers can be used. The personal care composition can comprise from about 0.5% to about 10% of a thickening polymer, from about 0.1% to about 4% of a thickening polymer, from about 0.5% to about 2% of a thickening polymer, and from about 0.7% to about 1% of a thickening polymer. The thickening polymer modifier may be a polyacrylate, polyacrylamide thickeners. The thickening polymer may be an anionic thickening polymer.

The personal care composition may comprise thickening polymers that are homopolymers based on acrylic acid, methacrylic acid or other related derivatives, non-limiting examples include polyacrylate, polymethacrylate, polyethylacrylate, and polyacrylamide.

The thickening polymers may be alkali swellable and hydrophobically-modified alkali swellable acrylic copolymers or methacrylate copolymers, non-limiting examples include acrylic acid/acrylonitrogens copolymer, acrylates/steareth-20 itaconate copolymer, acrylates/ceteth-20 itaconate copolymer, Acrylates/Aminoacrylates/C10-30 Alkyl PEG-20 Itaconate Copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, Acrylates/Palmeth-25 Acrylate Copolymer, Acrylic Acid/Acrylamidomethyl Propane Sulfonic Acid Copolymer, and acrylates/C10-C30 alkyl acrylate crosspolymer.

The thickening polymers may be soluble crosslinked acrylic polymers, a non-limiting example includes carbomers.

The thickening polymers may be an associative polymeric thickeners, non-limiting examples include: hydrophobically modified, alkali swellable emulsions, non-limiting examples include hydrophobically modified polypolyacrylates; hydrophobically modified polyacrylic acids, and hydrophobically modified polyacrylamides; hydrophobically modified polyethers wherein these materials may have a hydrophobe that can be selected from cetyl, stearyl, oleayl, and combinations thereof.

The thickening polymers may be used in combination with polyvinylpyrrolidone, crosslinked polyvinylpyrrolidone and derivatives. The thickening polymers may be combined with polyvinylalcohol and derivatives. The thickening polymers may be combined with polyethyleneimine and derivatives.

The thickening polymers may be combined with alginic acid based materials, non-limiting examples include sodium alginate, and alginic acid propylene glycol esters.

The thickening polymers may be used in combination with polyurethane polymers, non-limiting examples include: hydrophobically modified alkoxylated urethane polymers, non-limiting examples include PEG-150/decyl alcohol/SMDI copolymer, PEG-150/stearyl alcohol/SMDI copolymer, polyurethane-39.

The thickening polymers may be combined with an associative polymeric thickeners, non-limiting examples include: hydrophobically modified cellulose derivatives; and a hydrophilic portion of repeating ethylene oxide groups with repeat units from 10-300, from 30-200, and from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

The thickening polymers may be combined with cellulose and derivatives, non-limiting examples include microcrystalline cellulose, carboxymethylcelluloses, hydroxyethylcellulose, hydroxypropylcellulose, hydroxypropyl methylcellulose, methylcellulose, ethyl cellulose; nitro cellulose; cellulose sulfate; cellulose powder; hydrophobically modified celluloses.

The thickening polymers may be combined with a guar and guar derivatives, non-limting examples include hydroxypropyl guar, and hydroxypropyl guar hydroxypropyl trimonium chloride.

The thickening polymers may be combined with polyethylene oxide; polypropylene oxide; and POE-PPO copolymers.

The thickening polymers may be combined with polyalkylene glycols characterized by the general formula:

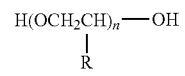

wherein R is hydrogen, methyl, or mixtures thereof, preferably hydrogen, and n is an integer having an average from 2,000-180,000, or from 7,000-90,000, or from 7,000-45,000. Non-limiting examples of this class include PEG-7M, PEG-14M, PEG-23M, PEG-25M, PEG-45M, PEG-90M, or PEG-100M.

The thickening polymers may be combined with water-swellable clays, non-limiting examples include laponite, bentolite, montmorillonite, smectite, and hectonite.

The thickening polymers may be combined with gums, non-limiting examples include xanthan gum, guar gum, hydroxypropyl guar gum, Arabia gum, tragacanth, galactan, carob gum, karaya gum, and locust bean gum.

The thickening polymers may be combined with, dibenzylidene sorbitol, karaggenan, pectin, agar, quince seed (Cydonia oblonga Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of thickening polymers include acrylamide/ammonium acrylate copolymer (and) polyisobutene (and) polysorbate 20; acrylamide/sodium acryloyldimethyl taurate copolymer/isohexadecane/polysorbate 80, ammonium acryloyldimethyltaurate/VP copolymer, Sodium Acrylate/Sodium Acryloyldimethyl Taurate Copolymer, acrylates copolymer, Acrylates Crosspolymer-4, Acrylates Crosspolymer-3, acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil; carbomer, sodium carbomer, crosslinked polyvinylpyrrolidone (PVP), polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, Acrylamide/Sodium Acryloyldimethyltaurate/Acrylic Acid Copolymer, sodium acrylate/acryloyldimethyltaurate/dimethylacrylamide, crosspolymer (and) isohexadecane (and) polysorbate 60, sodium polyacrylate. Exemplary commercially-available thickening polymers include ACULYN™ 28, ACULYN™ 88, ACULYN™ 33, ACULYN™ 22, ACULYN™ Excel, Carbopol® Aqua SF-1, Carbopol® ETD 2020, Carbopol® Ultrez 20, Carbopol® Ultrez 21, Carbopol® Ultrez 10, Carbopol® Ultrez 30, Carbopol® 1342, Carbopol® Aqua SF-2 Polymer, Sepigel™ 305, Simulgel™ 600, Sepimax Zen, Carbopol® SMART 1000, Rheocare® TTA, Rheomer® SC-Plus, STRUCTURE® PLUS, Aristoflex® AVC, Stabylen 30, and combinations thereof.

1. Water Miscible Solvents

The personal care composition may include water and non-limiting examples of polyhydric alcohols useful herein include propylene glycol, dipropylene glycol, butylenes glycol, hexylene glycol, glycerin, propane diol and mixtures thereof.

In present invention, the personal care composition may comprise a hydrotrope/viscosity modifier which is an alkali metal or ammonium salt of a lower alkyl benzene sulphonate such as sodium xylene sulphonate, sodium cumene sulphonate or sodium toluene sulphonate.

C. Scalp Health Agents

In the present invention, one or more scalp health agent may be added to provide scalp benefits in addition to soluble scalp health active efficacy provided by the soluble scalp health active. This group of materials is varied and provides a wide range of benefits including moisturization, barrier improvement, anti-fungal, anti-microbial and anti-oxidant, anti-itch, and sensates. Such scalp health agents include but are not limited to: vitamin E and F, salicylic acid, niacinamide, caffeine, panthenol, glycols, glycolic acid, PCA, PEGs, erythritol, glycerin, triclosan, lactates, hyaluronates, allantoin and other ureas, betaines, sorbitol, glutamates, xylitols, menthol, menthyl lactate, iso cyclomone, benzyl alcohol, a compound comprising the following structure:

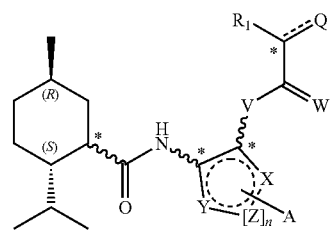

$R_1$ is selected from H, alkyl, amino alkyl, alkoxy;
$Q=H_2$, O, $—OR_1$, $—N(R_1)_2$, $—OPO(OR_1)_x$, $—PO(OR_1)_x$, $—P(OR_1)_x$ where x=1-2;
$V=NR_1$, O, $—OPO(OR_1)_x$, $—PO(OR_1)_x$, $—P(OR_1)_x$ where x=1-2;
$W=H_2$, O;
X, Y=independently selected from H, aryl, naphthyl for n=0;
X, Y=aliphatic $CH_2$ or aromatic CH for n≥1 and Z is selected from aliphatic $CH_2$, aromatic CH, or heteroatom;
A=lower alkoxy, lower alkylthio, aryl, subsitituted aryl or fused aryl; and stereochemistry is variable at the positions marked*.
and natural extracts/oils including peppermint, spearmint, argan, jojoba and aloe.

D. Optional Ingredients

In the present invention, the personal care composition may further comprise one or more optional ingredients, including benefit agents. Suitable benefit agents include, but are not limited to conditioning agents, cationic polymers, silicone emulsions, anti-dandruff agents, chelating agents, and natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof. In the present invention, a perfume may be present from about 0.5% to about 7%.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

1. Conditioning Agents

The conditioning agent of the personal care compositions can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference.

The silicone conditioning agents for use in the compositions of the present invention can have a viscosity, as measured at 25° C., from about 20 to about 2,000,000 centistokes ("csk"), from about 1,000 to about 1,800,000 csk, from about 10,000 to about 1,500,000 csk, and/or from about 20,000 to about 1,500,000 csk.

The dispersed silicone conditioning agent particles typically have a volume average particle diameter ranging from about 0.01 micrometer to about 0.10 micrometer. For small particle application to hair, the volume average particle diameters typically range from about 0.01 micrometer to about 0.10 micrometer, from about 0.01 micrometer to about 0.60 micrometer, from about 0.01 micrometer to about 0.30 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention may include, but are not limited to, emulsions of insoluble polysiloxanes prepared in accordance with the descriptions provided in U.S. Pat. No. 6,316,541 or 4,476,282 or U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having an internal phase viscosity from about 5 csk to about 500,000 csk. For example, the insoluble polysiloxane may have an internal phase viscosity less 400,000 csk, preferably less than 200,000 csk, more preferably from about 10,000 csk to about 180,000 csk. The insoluble polysiloxane can have an average particle size within the range from less than about 100 nm; from about 10 nm to about 100 nm. The average particle size may be within the range from about 15 nm to about 60 micron, or from about 30 nm to about 50 nm.

The average molecular weight of the insoluble polysiloxane, the internal phase viscosity of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

The conditioning agent of the personal care compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

2. Emusifiers

A variety of anionic and nonionic emulsifiers can be used in the personal care composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

3. Chelating Agents

The personal care composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Chelating agents can be incorporated in the compositions herein in amounts ranging from 0.001% to 10.0% by weight of the total composition, preferably 0.01% to 2.0%.

Nonlimiting chelating agent classes include carboxylic acids, aminocarboxylic acids, including aminocids, phosphoric acids, phosphonic acids, polyphosponic acids, polyethyleneimines, polyfunctionally-substituted aromatic, their derivatives and salts.

Nonlimiting chelating agents include the following materials and their salts. Ethylenediaminetetraacetic acid (EDTA), ethylenediaminetriacetic acid, ethylenediamine-N,N'-disuccinic acid (EDDS), ethylenediamine-N,N'-diglutaric acid (EDDG), salicylic acid, aspartic acid, glutamic acid, glycine, malonic acid, histidine, diethylenetriaminepentaacetate (DTPA), N-hydroxyethylethylenediaminetriacetate, nitrilotriacetate, ethylenediaminetetrapropionate, triethylenetetraaminehexaacetate, ethanoldiglycine, propylenediaminetetracetic acid (PDTA), methylglycinediacetic acid (MODA), diethylenetriaminepentaacetic acid, methylglycinediacetic acid (MGDA), N-acyl-N,N',N'-ethylenediaminetriacetic acid, nitrilotriacetic acid, ethylenediaminediglutaric acid (EDGA), 2-hydroxypropylenediamine disuccinic acid (HPDS), glycinamide-N, N-disuccinic acid (GADS), 2-hydroxypropylenediamine-N—N'-disuccinic acid (HPDDS), N-2-hydroxyethyl-N,N-diacetic acid, glyceryliminodiacetic acid, iminodiacetic acid-N-2-hydroxypropyl sulfonic acid, aspartic acid N-carboxymethyl-N-2-hydroxypropyl-3-sulfonic acid, alanine-N,N'-diacetic acid, aspartic acid-N,N'-diacetic acid, aspartic acid N-monoacetic acid, iminodisuccinic acid, diamine-N,N'-dipolyacid, monoamide-N,N'-dipolyacid, diaminoalkyldi(sulfosuccinic acids) (DDS), ethylenediamine-N—N'-bis (ortho-hydroxyphenyl acetic acid)), N,N'-bis(2-hydroxybenzyl)ethylenediamine-N, N'-diacetic acid, ethylenediaminetetraproprionate, triethylenetetraaminehexacetate, diethylenetriaminepentaacetate, dipicolinic acid, ethylenedicysteic acid (EDC), ethylenediamine-N,N'-bis(2-hydroxyphenylacetic acid) (EDDHA), glutamic acid diacetic acid (GLDA), hexadentateaminocarboxylate (HBED), polyethyleneimine, 1-hydroxydiphosphonate, aminotri(methylenephosphonic acid) (ATMP), nitrilotrimethylenephosphonate (NTP), ethylenediaminetetramethylenephosphonate, diethylenetriaminepentamethylenephosphonate (DTPMP), ethane-1-hydroxydiphosphonate (HEDP), 2-phosphonobutane-1,2,4-tricarboxylic acid, polyphosphoric acid, sodium tripolyphosphate, tetrasodium diphosphate, hexametaphosphoric acid, sodium metaphosphate, phosphonic acid and derivatives, Aminoalkylen-poly(alkylenphosphonic acid), aminotri(1-ethylphosphonic acid), ethylenediaminetetra(1-ethylphosphonic acid), aminotri(1-propylphosphonic acid), aminotri(isopropylphosphonic acid), ethylenediaminetetra(methylenephosphonic acid) (EDTMP), 1,2-dihydroxy-3,5-disulfobenzene.

4. Aqueous Carrier

The personal care compositions can be in the form of pourable liquids (under ambient conditions). Such compositions will therefore typically comprise a carrier, which is present at a level of from about 40% to about 85%, alternatively from about 45% to about 80%, alternatively from about 50% to about 75% by weight of the personal care composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the personal care compositions of the present invention may include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

The pH of the personal care composition may be from about pH of about 4.5 to about 6; from about from about 4 to about 6; from about 5 to about 6, from about 5.5 to about 6 and from about 4 to about 5.

G. Product Form

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos and personal cleansing products, and treatment products; and any other form that may be applied to hair.

Methods

Haze Method

This method is used as for haziness in transparent shampoos. The lower the haze value the more clear the shampoo formula appears. Haze is determined using a GretagMacbeth Model 7000 or newer spectrophotometer and the Xrite, Incorporated vendor-supplied software setting CHIOLL. Shampoo is centrifuged to remove any air bubbles that may be present. The shampoo is then put into a 1 cm path length cell (MacBeth P/N 27006250 or optically neutral equivalent that is 1¼ inch wide×2½ inch tall×10 mm and read by the spectrophotometer which calculates the Correlated Haze value; as well as, L*a*b values. Quantification of haze is by comparison of a sample of shampoo to a sample of air. Reference ASTM D 1003-00 Standard Test Method for Haze and Luminous Transmittance of Transparent Plastics.

The personal care composition of the present invention may have a haze value less than or equal to 25; a haze value of less than or equal 10; a haze value of less than or equal to 9; a haze value of less than or equal to 8; a haze value of less than or equal to 7 and a haze value less than or equal to 3.

Viscosity Measurement

Shampoo viscosities can be measured on a 2.5 mL sample using a cone and plate Brookfield RS rheometer with cone C75-1 at constant shear rate of 2 $s^{-1}$, at 27° C. at 3 mins.

Preparation of Shampoo Compositions

The shampoo compositions are prepared by adding surfactants, anti-dandruff agents, perfume, viscosity modifiers, cationic polymers and the remainder of the water with ample agitation to ensure a homogenous mixture. The mixture can be heated to 50-75° C. to speed the solubilization of the soluble agents, then cooled. Product pH may be adjusted as necessary to provide shampoo compositions of the present invention which are suitable for application to human hair and scalp, and may vary on the selection of particular detersive surfactants and/or other components.

Results

FIG. 1 data demonstrates that when the shampoo contains 13% Sodium Laureth-1 Sulfate (SLE1S) surfactant and 1% Sodium Deceth-1 Sulfate (C10E1) surfactant with only the anionic polymer Carbopol Aqua SF1 (SF1), the haze value decreases as the SF1 level increases resulting in the formula appearing clearer. In FIG. 1, the anionic polymer Carbopol Aqua SF1 levels evaluated are 0.7%, 2.0%, as well as 0.7% SF1 in combination with 0.4% Jaguar Excel cationic polymer.

Figure 2:
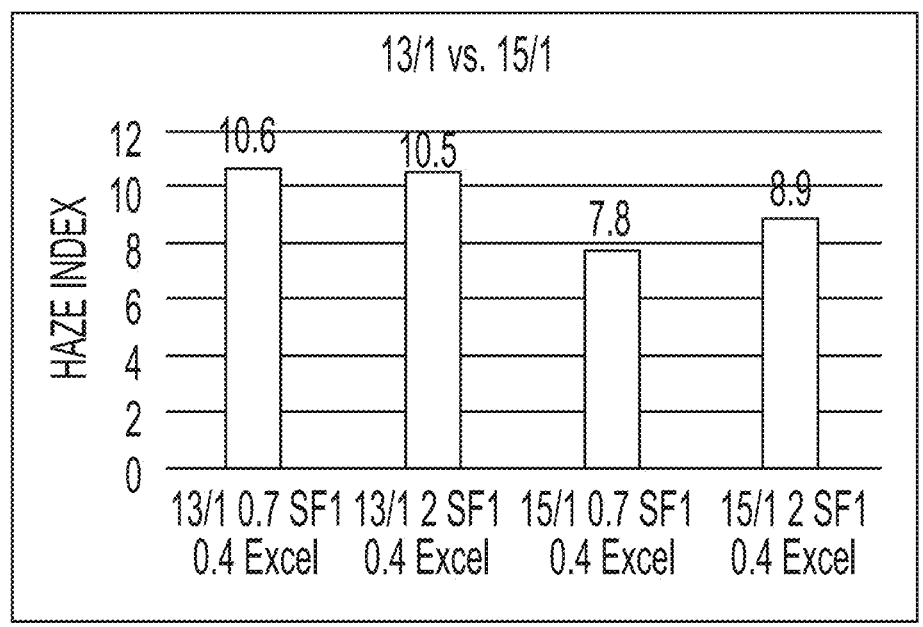
FIG. 2 is a graph showing anionic polymer combined with cationic polymer increasing anionic polymer Carbopol Aqua SF1 in some compositions.
Figure 3:
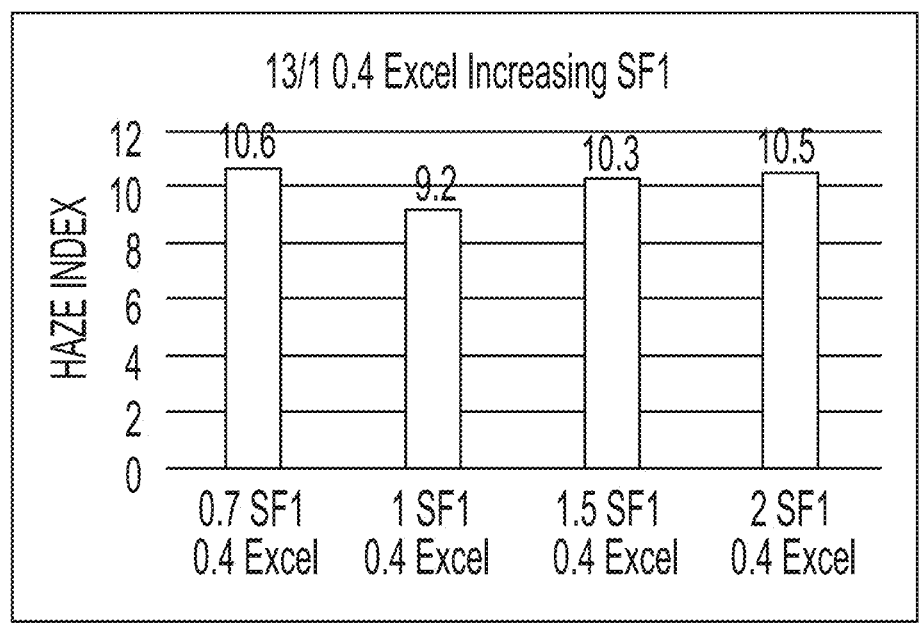
FIG. 3 is a graph showing anionic polymer combined with cationic polymer increasing anionic polymer Carbopol Aqua SF1 in some compositions.
Figure 4:
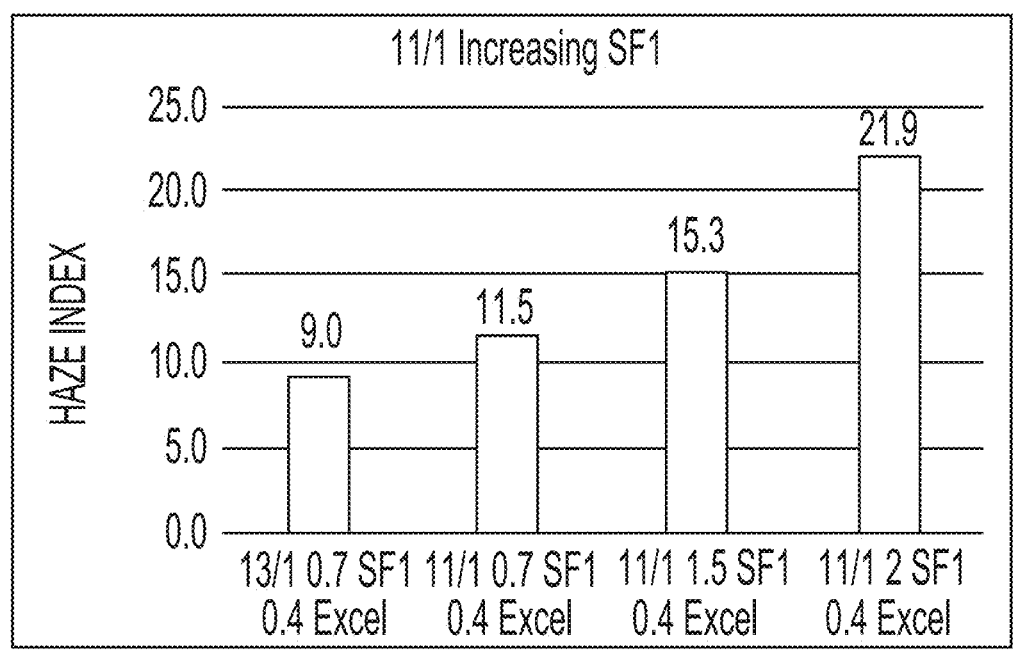
FIG. 4 is a graph showing anionic polymer combined with cationic polymer increasing anionic polymer Carbopol Aqua SF1 in some compositions.

FIGS. 2-4 demonstrate, with varying levels of surfactants, when the anionic polymer is combined with cationic polymer increasing anionic polymer Carbopol Aqua SF1 in some chassis does not decrease the haze value, and in other chassis it increases the haze value resulting in the formulas being similar in clarity or less clear.

FIG. 2 demonstrates 13% Sodium Laureth-1 Sulfate (SLE1S) surfactant and 1% Sodium Deceth-1 Sulfate (C10E1) in combination with 0.7% SF1 and 0.4% Jaguar Excel; as well as 13% Sodium Laureth-1 Sulfate (SLE1S) surfactant and 1% Sodium Deceth-1 Sulfate (C10E1) in combination with 2% SF1 and 0.4% Jaguar Excel. FIG. 2 further demonstrates 15% Sodium Laureth-1 Sulfate (SLE1S) surfactant and 1% Sodium Deceth-1 Sulfate (C10E1) in combination with 0.7% SF1 and 0.4% Jaguar Excel as well as 15% Sodium Laureth-1 Sulfate (SLE1S) surfactant and 1% Sodium Deceth-1 Sulfate (C10E1) in combination with 2% SF1 and 0.4% Jaguar Excel.

FIG. 3 demonstrates all samples containing 13% Sodium Laureth-1 Sulfate (SLE1S) surfactant and 1% Sodium Deceth-1 Sulfate (C10E1) in combination with increasing levels of SF1 and 0.4% Jaguar Excel, namely 0.7% SF1 with 0.4% Jaguar Excel; 1% SF1 with 0.4% Jaguar Excel; 1.5% SF1 with 0.4% Jaguar Excel and lastly 2% SF1 with 0.4% Jaguar Excel.

FIG. 4 demonstrates 13% Sodium Laureth-1 Sulfate (SLE1S) surfactant and 1% Sodium Deceth-1 Sulfate (C10E1) in combination with 0.7% SF1 and 0.4% Jaguar Excel; as well as 11% Sodium Laureth-1 Sulfate (SLE1S) surfactant and 1% Sodium Deceth-1 Sulfate (C10E1) in combination with 0.7% SF1 and 0.4% Jaguar Excel; and 11% Sodium Laureth-1 Sulfate (SLE1S) surfactant and 1% Sodium Deceth-1 Sulfate (C10E1) in combination with 1.5% SF1 and 0.4% Jaguar Excel; and 11% Sodium Laureth-1 Sulfate (SLE1S) surfactant and 1% Sodium Deceth-1 Sulfate (C10E1) in combination with 2% SF1 and 0.4% Jaguar Excel.

Non-Limiting Examples

The shampoo compositions illustrated in the following examples are prepared by conventional formulation and mixing methods. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified. The following examples are presented to further illustrate, but not to limit, the present invention

| Raw Material | Example 1 Target % | Example 2 Target % | Example 3 Target % | Example 4 Target % | Example 5 Target % | Example 6 Target % |
|---|---|---|---|---|---|---|
| Water | q.s. | q.s. | q.s. | q.s. | q.s. | q.s. |
| SLE1S[1] | 13.00 | 13.00 | 13.00 | 13.00 | 15.00 | 15.00 |
| C10E1[2] | 1.00 | 1.00 | 1.00 | 1.00 | 1.00 | 1.00 |
| Acrylate Copolymer[3] | 0.70 | 0.70 | 2.00 | 2.00 | 0.70 | 2.00 |
| Piroctone olamine[4] | 0.50 | 0.50 | 0.50 | 0.50 | 0.50 | 0.50 |
| Guar Hydroxypropyltrimonium Chloride[5] | — | 0.40 | — | 0.40 | 0.40 | 0.40 |
| EDTA[6] | 0.13 | 0.13 | 0.13 | 0.13 | 0.13 | 0.13 |
| Sodium Benzoate[7] | 0.25 | 0.25 | 0.25 | 0.25 | 0.25 | 0.25 |
| Sodium Chloride[8] | 1.82 | 0.8 | 0.65 | 0.00 | 0.85 | 0.00 |
| Citric Acid[9] | 0.57 | 0.48 | 0.44 | 0.49 | 0.50 | 0.52 |
| Methylchloroisothiazolinone/ Methylisothiazolinone[10] | 0.000005 | 0.000005 | 0.000005 | 0.000005 | 0.000005 | 0.000005 |
| Fragrance | 1.10 | 1.10 | 1.10 | 1.10 | 1.10 | 1.10 |
| Sodium Hydroxide[11] | 0.1 | — | — | — | — | — |
| Haze Value | 5.3 | 10.6 | 4.5 | 10.5 | 7.8 | 8.3 |
| Viscosity (cps) | 8,234 | 6,598 | 10,747 | 11,321 | 11,557 | 13,451 |
| pH | 5.38 | 5.52 | 5.50 | 5.46 | 5.51 | 5.49 |

| Raw Material | Example 2 Target % | Example 7 Target % | Example 8 Target % | Example 4 Target % |
|---|---|---|---|---|
| Water | q.s. | q.s. | q.s. | q.s. |
| SLE1S[1] | 13.00 | 13.00 | 13.00 | 13.00 |
| C10E1[2] | 1.00 | 1.00 | 1.00 | 1.00 |
| Acrylate Copolymer[3] | 0.70 | 1.00 | 1.50 | 2.00 |
| Piroctone olamine[4] | 0.50 | 0.50 | 0.50 | 0.50 |
| Guar Hydroxypropyltrimonium Chloride[5] | 0.40 | 0.40 | 0.40 | 0.40 |
| EDTA[6] | 0.13 | 0.13 | 0.13 | 0.13 |
| Sodium Benzoate[7] | 0.25 | 0.25 | 0.25 | 0.25 |
| Sodium Chloride[8] | 0.8 | 0.75 | 0.41 | 0.00 |
| Citric Acid[9] | 0.48 | 0.54 | 0.46 | 0.49 |
| Methylchloroisothiazolinone/ Methylisothiazolinone[10] | 0.000005 | 0.000005 | 0.000005 | 0.000005 |
| Fragrance | 1.10 | 1.10 | 1.10 | 1.10 |
| Sodium Hydroxide[11] | — | 0.04 | — | — |
| Haze Value | 10.6 | 9.2 | 10.3 | 10.5 |
| Viscosity (cps) | 6,598 | 9,350 | 9,020 | 11,321 |
| pH | 5.52 | 5.40 | 5.53 | 5.46 |

| Raw Material | Example 9 Target % | Example 10 Target % | Example 11 Target % | Example 12 Target % |
|---|---|---|---|---|
| Water | q.s. | q.s. | q.s. | q.s. |
| SLE1S[1] | 13.00 | 11.00 | 11.00 | 11.00 |
| C10E1[2] | 1.00 | 1.00 | 1.00 | 1.00 |
| Acrylate Copolymer[3] | 0.70 | 0.70 | 1.50 | 2.00 |

-continued

|  |  |  |  |  |
|---|---|---|---|---|
| Piroctone olamine[4] | 0.50 | 0.50 | 0.50 | 0.50 |
| Guar Hydroxypropyltrimonium Chloride[5] | 0.40 | 0.40 | 0.40 | 0.40 |
| EDTA[6] | 0.13 | 0.13 | 0.13 | 0.13 |
| Sodium Benzoate[7] | 0.25 | 0.25 | 0.25 | 0.25 |
| Sodium Chloride[8] | 1.08 | 1.26 | 0.68 | 0.27 |
| Citric Acid[9] | 0.50 | 0.49 | 0.46 | 0.43 |
| Methylchloroisothiazolinone/ Methylisothiazolinone[10] | 0.000005 | 0.000005 | 0.000005 | 0.000005 |
| Fragrance | 1.10 | 1.10 | 1.10 | 1.10 |
| Haze Value | 9.0 | 11.5 | 15.3 | 21.9 |
| Viscosity (cps) | 9,819 | 8,896 | 10,060 | 10,527 |
| pH | 5.45 | 5.31 | 5.38 | 5.44 |

[1]Sodium Laureth-1 Sulfate at 26% active, supplier: P&G
[2]Sodium Deceth-1 Sulfate at 35% active, supplier P&G
[3]Carbopol Aqua SF1-1 at 30% active, supplier Lubrizol
[4]Octopirox; supplier: Clariant
[5]Jaguar Excel, Solvay Novecare
[6]Dissolvine 220-S at 84% active, supplier: Akzo Nobel
[7]Sodium Benzoate Dense NF/FCC, supplier: Emerald Performance Materials
[8]Sodium Chloride, supplier: Morton; level adjustable to achieve target viscosity
[9]Citric Acid Anhydrous, supplier: Archer Daniels Midland; level adjustable to achieve target pH
[10]Kathon CG at 1.5% active, supplier: Rohm & Haas
[11]Sodium Hydroxide, Ka Steel Chemicals Inc; level adjustable to achieve target pH FIGS. 5-8 data demonstrates that the clarity increases (haze value decreases) as the total surfactant increases and/or the Sodium Deceth-1 Sulfate (C10E1) surfactant increases.

Figure 5:
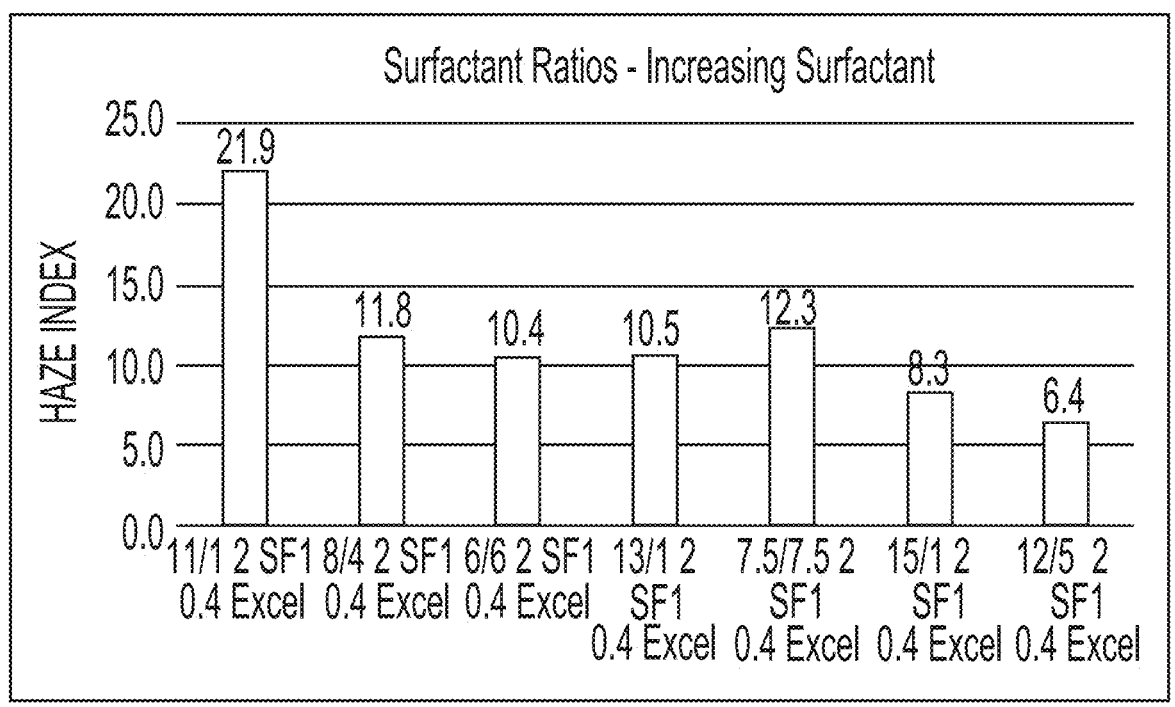
FIG. 5 is a graph demonstrating that the clarity increases (haze value decreases) as the total surfactant increases and/or the Sodium Deceth-1 Sulfate (C10E1) surfactant increases.

FIG. 5 demonstrates 11% Sodium Laureth-1 Sulfate (SLE1S) surfactant and 1% Sodium Deceth-1 Sulfate (C10E1) in combination with 2% SF1 and 0.4% Jaguar Excel. FIG. 5 further demonstrates 8% Sodium Laureth-1 Sulfate (SLE1S) surfactant and 4% Sodium Deceth-1 Sulfate (C10E1) in combination with 2% SF1 and 0.4% Jaguar Excel. FIG. 5 further demonstrates 6% Sodium Laureth-1 Sulfate (SLE1S) surfactant and 6% Sodium Deceth-1 Sulfate (C10E1) in combination with 2% SF1 and 0.4% Jaguar Excel. FIG. 5 further demonstrates 13% Sodium Laureth-1 Sulfate (SLE1S) surfactant and 1% Sodium Deceth-1 Sulfate (C10E1) in combination with 2% SF1 and 0.4% Jaguar Excel. FIG. 5 further demonstrates 7.5% Sodium Laureth-1 Sulfate (SLE1S) surfactant and 7.5% Sodium Deceth-1 Sulfate (C10E1) in combination with 2% SF1 and 0.4% Jaguar Excel. FIG. 5 further demonstrates 15% Sodium Laureth-1 Sulfate (SLE1S) surfactant and 1% Sodium Deceth-1 Sulfate (C10E1) in combination with 2% SF1 and 0.4% Jaguar Excel. Lastly, FIG. 5 demonstrates 12% Sodium Laureth-1 Sulfate (SLE1S) surfactant and 5% Sodium Deceth-1 Sulfate (C10E1) in combination with 2% SF1 and 0.4% Jaguar Excel.

Figure 6:
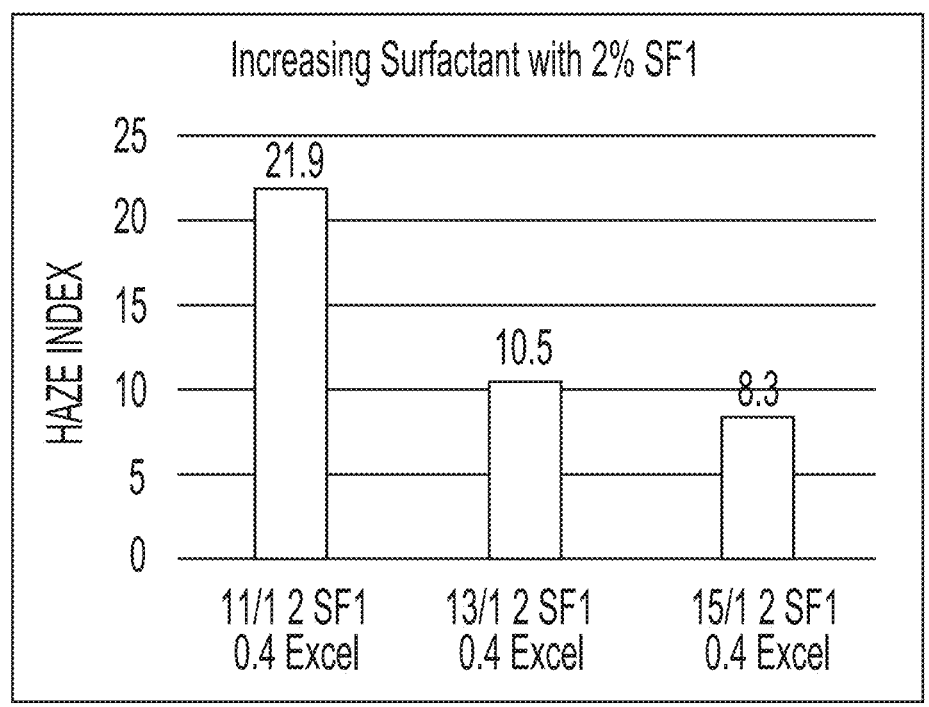
FIG. 6 is a graph demonstrating that the clarity increases (haze value decreases) as the total surfactant increases and/or the Sodium Deceth-1 Sulfate (C10E1) surfactant increases.

FIG. 6 demonstrates 11% Sodium Laureth-1 Sulfate (SLE1S) surfactant and 1% Sodium Deceth-1 Sulfate (C10E1) in combination with 2% SF1 and 0.4% Jaguar Excel. FIG. 6 further demonstrates 13% Sodium Laureth-1 Sulfate (SLE1S) surfactant and 1% Sodium Deceth-1 Sulfate (C10E1) in combination with 2% SF1 and 0.4% Jaguar Excel. Lastly, FIG. 6 demonstrates 15% Sodium Laureth-1 Sulfate (SLE1S) surfactant and 1% Sodium Deceth-1 Sulfate (C10E1) in combination with 2% SF1 and 0.4% Jaguar Excel.

Figure 7:
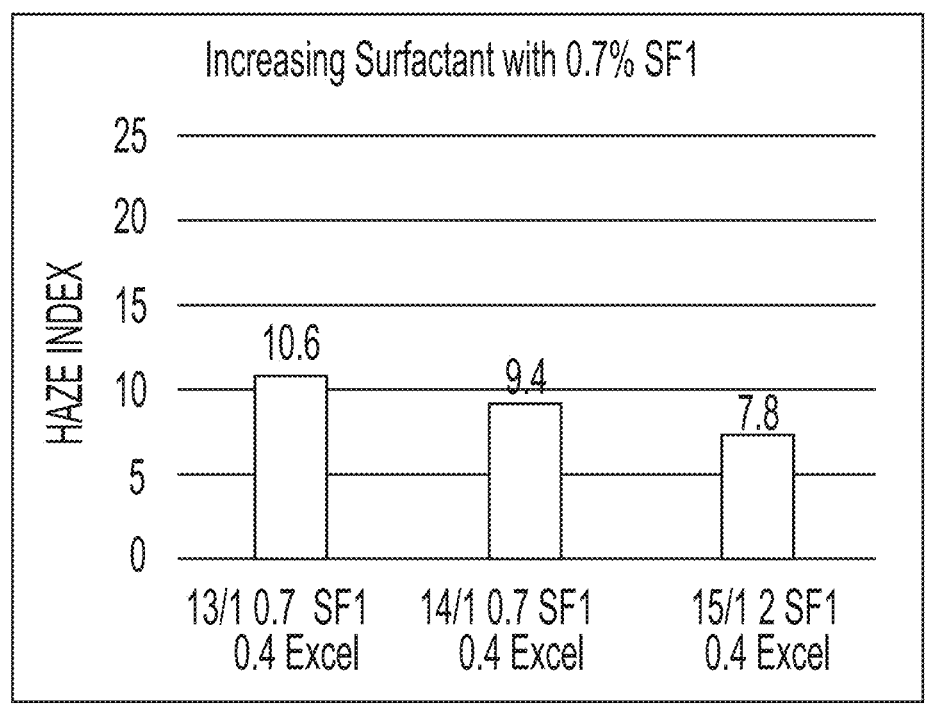
FIG. 7 is a graph demonstrating that the clarity increases (haze value decreases) as the total surfactant increases and/or the Sodium Deceth-1 Sulfate (C10E1) surfactant increases.

FIG. 7 demonstrates 13% Sodium Laureth-1 Sulfate (SLE1S) surfactant and 1% Sodium Deceth-1 Sulfate (C10E1) in combination with 0.7% SF1 and 0.4% Jaguar Excel. FIG. 7 demonstrates 14% Sodium Laureth-1 Sulfate (SLE1S) surfactant and 1% Sodium Deceth-1 Sulfate (C10E1) in combination with 0.7% SF1 and 0.4% Jaguar Excel. FIG. 7 lastly demonstrates 15% Sodium Laureth-1 Sulfate (SLE1S) surfactant and 1% Sodium Deceth-1 Sulfate (C10E1) in combination with 0.7% SF1 and 0.4% Jaguar Excel.

Figure 8:
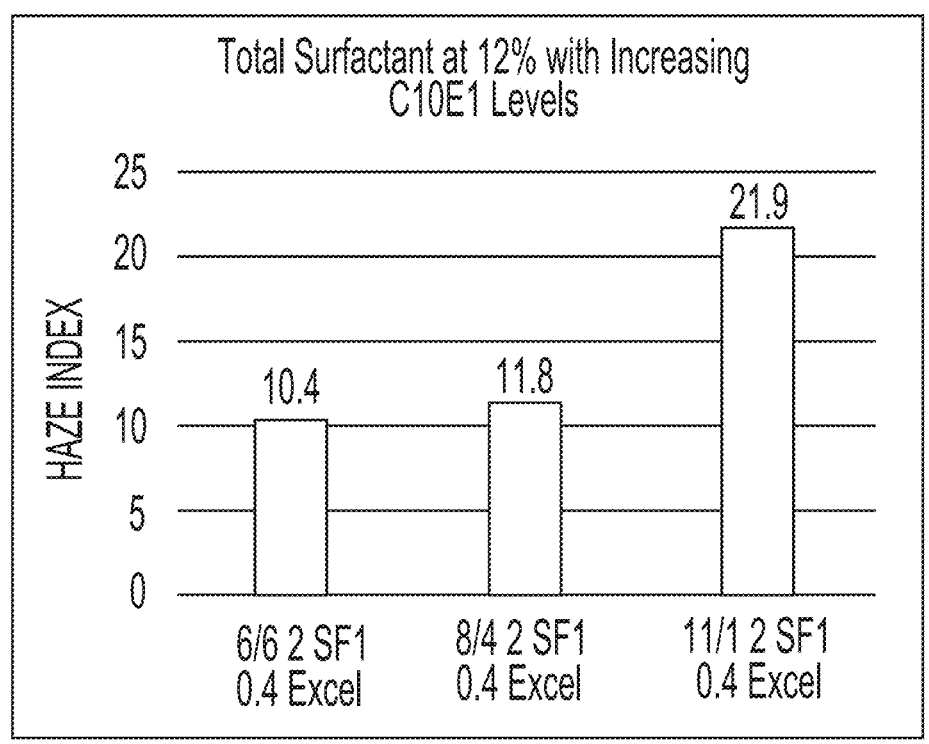
FIG. 8 is a graph demonstrating that the clarity increases (haze value decreases) as the total surfactant increases and/or the Sodium Deceth-1 Sulfate (C10E1) surfactant increases.

FIG. 8 demonstrates 6% Sodium Laureth-1 Sulfate (SLE1S) surfactant and 6% Sodium Deceth-1 Sulfate (C10E1) in combination with 2% SF1 and 0.4% Jaguar Excel. FIG. 8 demonstrates 8% Sodium Laureth-1 Sulfate (SLE1S) surfactant and 4% Sodium Deceth-1 Sulfate (C10E1) in combination with 2% SF1 and 0.4% Jaguar Excel. Lastly, FIG. 8 demonstrates 11% Sodium Laureth-1 Sulfate (SLE1S) surfactant and 1% Sodium Deceth-1 Sulfate (C10E1) in combination with 2% SF1 and 0.4% Jaguar Excel

| Raw Material | Example 12 Target % | Example 13 Target % | Example 14 Target % | Example 4 Target % | Example 15 Target % | Example 6 Target % | Example 16 Target % |
|---|---|---|---|---|---|---|---|
| Water | q.s. | q.s. | q.s. | q.s. | q.s. | q.s. | q.s. |
| SLE1S[1] | 11.00 | 8.00 | 6.00 | 13.00 | 7.50 | 15.00 | 12.00 |
| C10E1[2] | 1.00 | 4.00 | 6.00 | 1.00 | 7.50 | 1.00 | 5.00 |
| Acrylate Copolymer[3] | 2.00 | 2.00 | 2.00 | 2.00 | 2.00 | 2.00 | 2.00 |
| Piroctone olamine[4] | 0.50 | 0.50 | 0.50 | 0.50 | 0.50 | 0.50 | 0.50 |
| Guar Hydroxypropyltrimonium Chloride[5] | 0.40 | 0.40 | 0.40 | 0.40 | 0.40 | 0.40 | 0.40 |
| EDTA[6] | 0.13 | 0.13 | 0.13 | 0.13 | 0.13 | 0.13 | 0.13 |
| Sodium Benzoate[7] | 0.25 | 0.25 | 0.25 | 0.25 | 0.25 | 0.25 | 0.25 |
| Sodium Chloride[8] | 0.27 | 0.99 | 0.99 | 0.00 | 0.99 | 0.00 | 0.99 |

| | | | | | | | |
|---|---|---|---|---|---|---|---|
| Citric Acid[9] | 0.43 | 0.41 | 0.43 | 0.49 | 0.49 | 0.52 | 0.53 |
| Methylchloroisothiazolinone/Methylisothiazolinone[10] | 0.000005 | 0.000005 | 0.000005 | 0.000005 | 0.000005 | 0.000005 | 0.000005 |
| Fragrance | 1.10 | 1.10 | 1.10 | 1.10 | 1.10 | 1.10 | 1.10 |
| Haze Value | 21.9 | 11.8 | 10.4 | 10.5 | 12.3 | 8.3 | 6.4 |
| Viscosity (cps) | 10,527 | 11,228 | 9,480 | 11,321 | 9,338 | 13,451 | 15,985 |
| pH | 5.44 | 5.51 | 5.49 | 5.46 | 5.54 | 5.49 | 5.47 |

| Raw Material | Example 12 Target % | Example 4 Target % | Example 6 Target % | Example 2 Target % | Example 17 Target % | Example 5 Target % |
|---|---|---|---|---|---|---|
| Water | q.s. | q.s. | q.s. | q.s. | q.s. | q.s. |
| SLE1S[1] | 11.00 | 13.00 | 15.00 | 13.00 | 14.00 | 15.00 |
| C10E1[2] | 1.00 | 1.00 | 1.00 | 1.00 | 1.00 | 1.00 |
| Acrylate Copolymer[3] | 2.00 | 2.00 | 2.00 | 0.70 | 0.70 | 0.70 |
| Piroctone olamine[4] | 0.50 | 0.50 | 0.50 | 0.50 | 0.50 | 0.50 |
| Guar Hydroxypropyltrimonium Chloride[5] | 0.40 | 0.40 | 0.40 | 0.40 | 0.40 | 0.40 |
| EDTA[6] | 0.13 | 0.13 | 0.13 | 0.13 | 0.13 | 0.13 |
| Sodium Benzoate[7] | 0.25 | 0.25 | 0.25 | 0.25 | 0.25 | 0.25 |
| Sodium Chloride[8] | 0.27 | 0.00 | 0.00 | 0.8 | 0.90 | 0.85 |
| Citric Acid[9] | 0.43 | 0.49 | 0.52 | 0.48 | 0.56 | 0.50 |
| Methylchloroisothiazolinone/Methylisothiazolinone[10] | 0.000005 | 0.000005 | 0.000005 | 0.000005 | 0.000005 | 0.000005 |
| Fragrance | 1.10 | 1.10 | 1.10 | 1.10 | 1.10 | 1.10 |
| Sodium Hydroxide[11] | — | — | — | — | 0.04 | — |
| Haze Value | 21.9 | 10.5 | 8.3 | 10.6 | 9.4 | 7.8 |
| Viscosity (cps) | 10,527 | 11,321 | 13,451 | 6,598 | 10,573 | 11,557 |
| pH | 5.44 | 5.46 | 5.49 | 5.52 | 5.45 | 5.51 |

[1]Sodium Laureth-1 Sulfate at 26% active, supplier: P&G
[2]Sodium Deceth-1 Sulfate at 35% active, supplier P&G
[3]Carbopol Aqua SF1-1 at 30% active, supplier Lubrizol
[4]Octopirox; supplier: Clariant
[5]Jaguar Excel, Solvay Novecare
[6]Dissolvine 220-S at 84% active, supplier: Akzo Nobel
[7]Sodium Benzoate Dense NF/FCC, supplier: Emerald Performance Materials
[8]Sodium Chloride, supplier: Morton; level adjustable to achieve target viscosity
[9]Citric Acid Anhydrous, supplier: Archer Daniels Midland; level adjustable to achieve target pH
[10]Kathon CG at 1.5% active, supplier: Rohm & Haas
[11]Sodium Hydroxide, Ka Steel Chemicals Inc; level adjustable to achieve target pH FIG. 9 data demonstrates that when pH decreases the formula haze value decreases and appears clearer.

Figure 9:
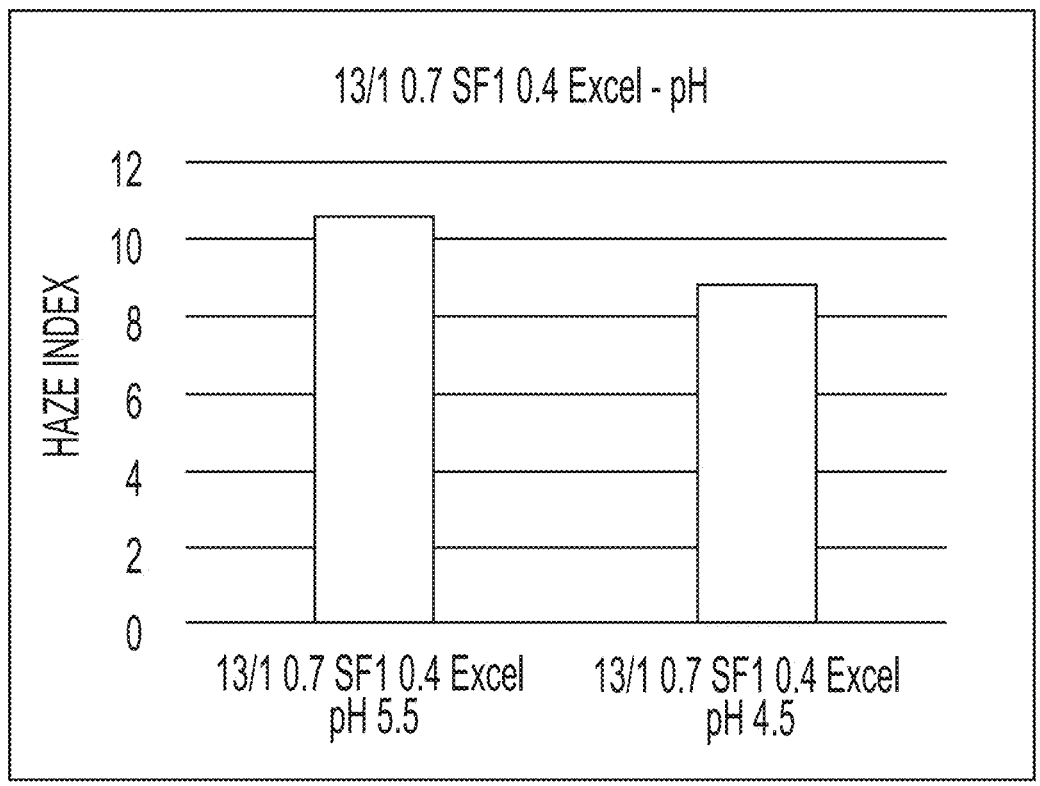
FIG. 9 is a graph demonstrating that when pH decreases the formula haze value decreases and appears clearer.

FIG. 9 demonstrates 13% Sodium Laureth-1 Sulfate (SLE1S) surfactant and 1% Sodium Deceth-1 Sulfate (C10E1) in combination with 0.7% SF1 and 0.4% Jaguar Excel at pH 5.5. Lastly, FIG. 9 demonstrates 13% Sodium Laureth-1 Sulfate (SLE1S) surfactant and 1% Sodium Deceth-1 Sulfate (C10E1) in combination with 0.7% SF1 and 0.4% Jaguar Excel at pH 4.5

| Raw Material | Example 2 Target % | Example 18 Target % |
|---|---|---|
| Water | q.s. | q.s. |
| SLE1S[1] | 13.00 | 13.00 |
| C10E1[2] | 1.00 | 1.00 |
| Acrylate Copolymer[3] | 0.70 | 0.70 |
| Piroctone olamine[4] | 0.50 | 0.50 |
| Guar Hydroxypropyltrimonium Chloride[5] | 0.40 | 0.40 |
| EDTA[6] | 0.13 | 0.13 |
| Sodium Benzoate[7] | 0.25 | 0.25 |
| Sodium Chloride[8] | 0.80 | 0.98 |
| Citric Acid[9] | 0.48 | 0.85 |
| Methylchloroisothiazolinone/Methylisothiazolinone[10] | 0.000005 | 0.000005 |
| Fragrance | 1.10 | 1.10 |
| Haze Value | 10.6 | 8.6 |
| Viscosity (cps) | 6,598 | 12,770 |
| pH | 5.52 | 4.57 |

[1]Sodium Laureth-1 Sulfate at 26% active, supplier: P&G
[2]Sodium Deceth-1 Sulfate at 35% active, supplier P&G
[3]Carbopol Aqua SF1-1 at 30% active, supplier Lubrizol
[4]Octopirox; supplier: Clariant
[5]Jaguar Excel, Solvay Novecare
[6]Dissolvine 220-S at 84% active, supplier: Akzo Nobel
[7]Sodium Benzoate Dense NF/FCC, supplier: Emerald Performance Materials
[8]Sodium Chloride, supplier: Morton; level adjustable to achieve target viscosity
[9]Citric Acid Anhydrous, supplier: Archer Daniels Midland; level adjustable to achieve target pH
[10]Kathon CG at 1.5% active, supplier: Rohm & Haas FIG. 10 data demonstrates that changing the cationic polymer type can impact the clarity. The data demonstrates that the cationic polymers LR400, LR30M, JR 30M, JR400 and Excel all result in improved clarity.

Figure 10:
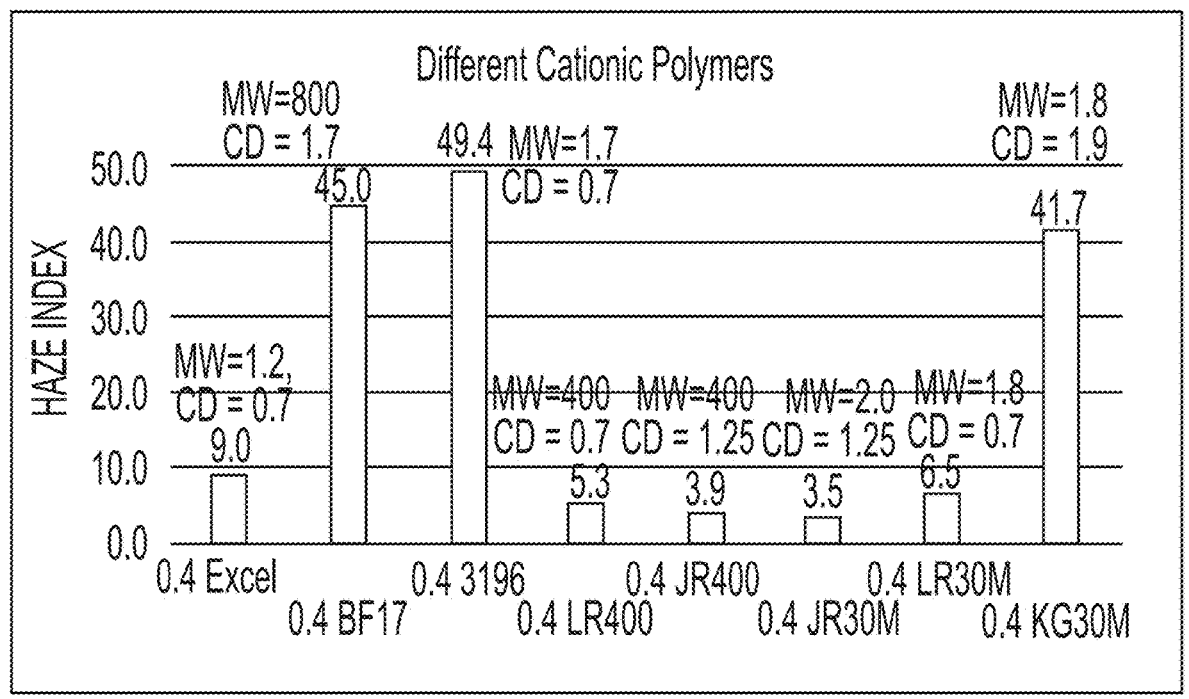
FIG. 10 is a graph demonstrating changing the cationic polymer type can impact the clarity.

FIG. 10 demonstrates 0.4% Jaguar Excel molecular weight (MW)=1.2 million g/mol, charge density (CD)=0.7 meq/g); 0.4% N-Hance BF17 (MW=800,000 g/mol, CD=1.7 meq/g), 0.4 N-Hance 3196 (MW=1.7 million g/mol, CD=0.7 meq/g); 0.4% LR400 (MW=400,000 g/mol, CD=0.7 meq/g); 0.4% JR400 (MW=400,000 g/mol, CD=1.25 meq/g); 0.4% JR30M (MW=2.0 million g/mol, CD=1.25 meq/g); 0.4% LR30M (MW=1.8 million g/mol, CD=0.7 meq/g) and lastly 0.4 KG30M (MW 1.8 million g/mol, CD=1.9 meq/g); each cationic polymer type is in combination with 13% Sodium Laureth-1 Sulfate (SLE1S) surfactant and 1% Sodium Deceth-1 Sulfate (C10E1) and with 0.7% SF1.

| Raw Material | Example 9 Target % | Example 19 Target % | Example 20 Target % | Example 21 Target % | Example 22 Target % | Example 23 Target % | Example 24 Target % | Example 25 Target % |
|---|---|---|---|---|---|---|---|---|
| Water | q.s. | q.s. | q.s. | q.s. | q.s. | q.s. | q.s. | q.s. |
| SLE1S[1] | 13.00 | 13.00 | 13.00 | 13.00 | 13.00 | 13.00 | 13.00 | 13.00 |
| C10E1[2] | 1.00 | 1.00 | 1.00 | 1.00 | 1.00 | 1.00 | 1.00 | 1.00 |
| Acrylate Copolymer[3] | 0.70 | 0.70 | 0.70 | 0.70 | 0.70 | 0.70 | 0.70 | 0.70 |
| Piroctone olamine[4] | 0.50 | 0.50 | 0.50 | 0.50 | 0.50 | 0.50 | 0.50 | 0.50 |
| Guar Hydroxypropyltrimonium Chloride[5] | 0.40 | — | — | — | — | — | — | — |
| Polyquaternium-10[6] | — | — | 0.40 | — | — | — | — | — |
| Polyquaternium-10[7] | — | 0.40 | — | — | — | — | — | — |
| Polyquaternium-10[8] | — | — | — | 0.40 | — | — | — | — |
| Polyquaternium-10[9] | — | — | — | — | 0.40 | — | — | — |
| Guar Hydroxypropyltrimonium Chloride[10] | — | — | — | — | — | — | 0.40 | — |
| Guar Hydroxypropyltrimonium Chloride[11] | — | — | — | — | — | — | — | 0.40 |
| Polyquaternium-10[12] | — | — | — | — | — | 0.40 | — | — |
| EDTA[13] | 0.13 | 0.13 | 0.13 | 0.13 | 0.13 | 0.13 | 0.13 | 0.13 |
| Sodium Benzoate[14] | 0.25 | 0.25 | 0.25 | 0.25 | 0.25 | 0.25 | 0.25 | 0.25 |
| Sodium Chloride[15] | 1.08 | 1.39 | 1.39 | 1.38 | 1.38 | 0.49 | 0.99 | 1.00 |
| Citric Acid[16] | 0.50 | 0.49 | 0.48 | 0.59 | 0.52 | 0.67 | 0.55 | 0.49 |
| Methylchloroisothiazolinone/Methylisothiazolinone[17] | 0.000005 | 0.000005 | 0.000005 | 0.000005 | 0.000005 | 0.000005 | 0.000005 | 0.000005 |
| Fragrance | 1.10 | 1.10 | 1.10 | 1.10 | 1.10 | 1.10 | 1.10 | 1.10 |
| Sodium Hydroxide[18] | — | — | — | 0.12 | — | — | 0.11 | — |
| Haze Value | 9.0 | 5.3 | 3.5 | 6.5 | 3.9 | 41.7 | 45.0 | 49.4 |
| Viscosity (cps) | 9,819 | 8,704 | 17,641 | 15,628 | 9,549 | 4,970 | 10,858 | 8,966 |
| pH | 5.45 | 5.51 | 5.56 | 5.54 | 5.36 | 4.99 | 5.53 | 5.50 |

[1] Sodium Laureth-1 Sulfate at 26% active, supplier: P&G
[2] Sodium Deceth-1 Sulfate at 35% active, supplier P&G
[3] Carbopol Aqua SF-1 at 30% active, supplier Lubrizol
[4] Octopirox; supplier: Clariant
[5] Jaguar Excel, Solvay Novecare
[6] JR30M, supplier Dow Chemical
[7] LR400 supplier Dow Chemical
[8] LR30M, supplier Dow Chemical
[9] JR400, supplier Dow Chemical
[10] N-Hance BF17, supplier Ashland
[11] N-Hance 3196, supplier Ashland
[12] KG30M, supplier Dow Chemical
[13] Dissolvine 220-S at 84% active, supplier: Akzo Nobel
[14] Sodium Benzoate Dense NF/FCC, supplier: Emerald Performance Materials
[15] Sodium Chloride, supplier: Morton; level adjustable to achieve target viscosity
[16] Citric Acid Anhydrous, supplier: Archer Daniels Midland; level adjustable to achieve target pH
[17] Kathon CG at 1.5% active, supplier: Rohm & Haas
[18] Sodium Hydroxide, Ka Steel Chemicals Inc; level adjustable to achieve target pH FIG. 11 data demonstrates that pH adjusting the formula to a pH of about 5.5-5.6 before adding perfume improves the haze value of the formula.

Figure 11:
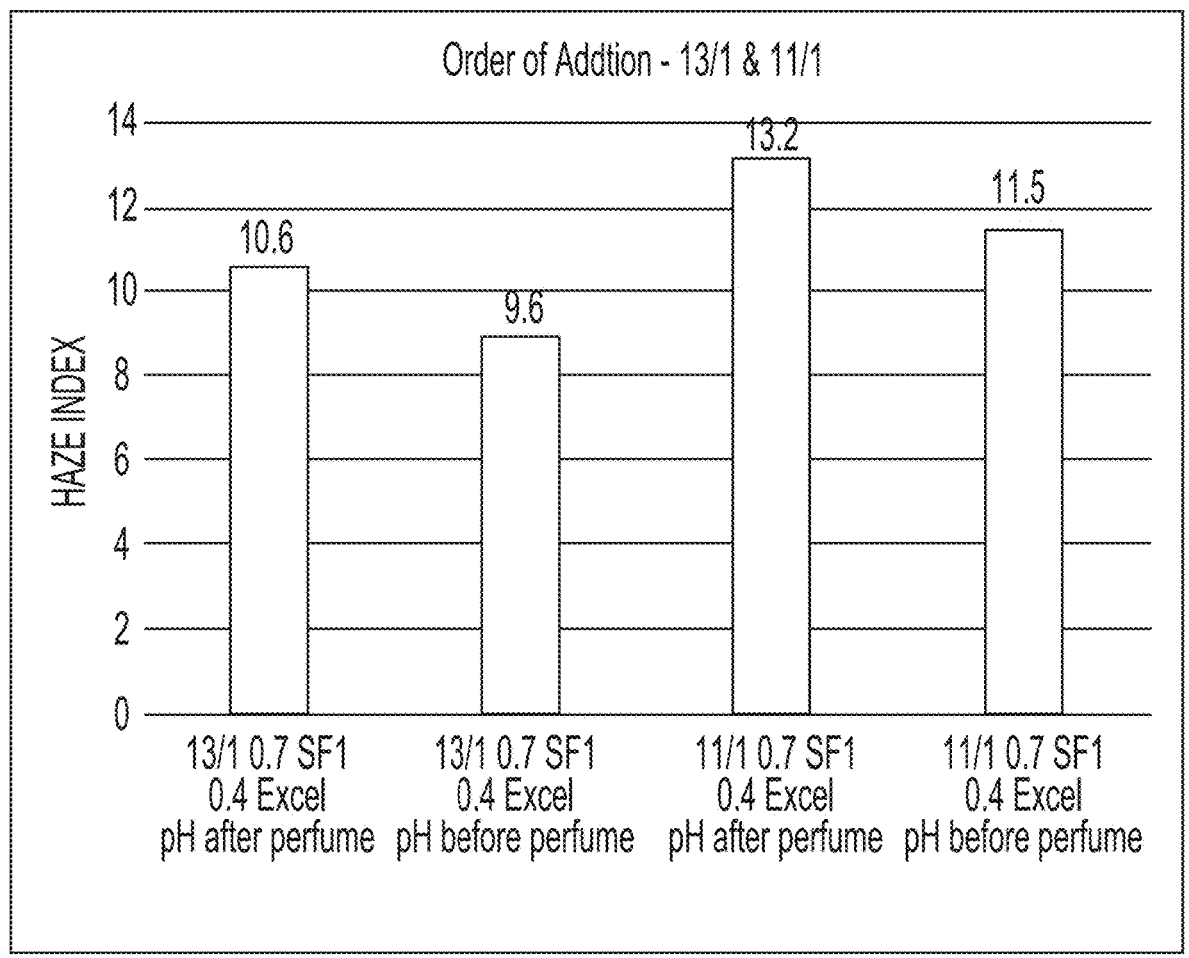
FIG. 11 is a graph demonstrating pH adjusting the formula to a pH of about 5.5-5.6 before adding perfume improves the haze value of the formula.

FIG. 11 demonstrates 13% Sodium Laureth-1 Sulfate (SLE1S) surfactant and 1% Sodium Deceth-1 Sulfate (C10E1) in combination with 0.7% SF1 and 0.4% Jaguar Excel with pH adjusted to 5.5-5.6 before adding perfume. FIG. 11 demonstrates 11% Sodium Laureth-1 Sulfate (SLE1S) surfactant and 1% Sodium Deceth-1 Sulfate (C10E1) in combination with 0.7% SF1 and 0.4% Jaguar Excel with pH adjusted to 5.5-5.6 after adding perfume. FIG. 11 demonstrates 11% Sodium Laureth-1 Sulfate (SLE1S) surfactant and 1% Sodium Deceth-1 Sulfate (C10E1) in combination with 0.7% SF1 and 0.4% Jaguar Excel with pH adjusted to 5.5-5.6 before adding perfume. Lastly, FIG. 11 demonstrates 11% Sodium Laureth-1 Sulfate (SLE1S) surfactant and 1% Sodium Deceth-1 Sulfate (C10E1) in combination with 0.7% SF1 and 0.4% Jaguar Excel with pH adjusted to 5.5-5.6 before adding perfume.

| Raw Material | Example 2 Target % | Example 9 Target % | Example 210 Target % | Example 6 Target % |
|---|---|---|---|---|
| Water | q.s. | q.s. | q.s. | q.s. |
| SLE1S[1] | 13.00 | 13.00 | 11.00 | 11.00 |
| C10E1[2] | 1.00 | 1.00 | 1.00 | 1.00 |
| Acrylate Copolymer[3] | 0.70 | 0.70 | 0.70 | 0.70 |
| Piroctoneolamine[4] | 0.50 | 0.50 | 0.50 | 0.50 |
| Guar Hydroxypropyltrimonium Chloride[5] | 0.40 | 0.40 | 0.40 | 0.40 |
| EDTA[6] | 0.13 | 0.13 | 0.13 | 0.13 |
| Sodium Benzoate[7] | 0.25 | 0.25 | 0.25 | 0.25 |
| Sodium Chloride[8] | 0.80 | 1.08 | 1.02 | 1.26 |
| Citric Acid[9] | 0.48 | 0.50 | 0.44 | 0.49 |
| Methylchloroisothiazolinone/ Methylisothiazolinonel[10] | 0.000005 | 0.000005 | 0.000005 | 0.000005 |
| Fragrance | 1.10 | 1.10 | 1.10 | 1.10 |
| Haze Value | 10.6 | 9.0 | 13.2 | 11.5 |
| Viscosity (cps) | 6,598 | 9,819 | 5,966 | 8,896 |
| pH | 5.52 | 5.45 | 5.48 | 5.31 |

Figure 12:
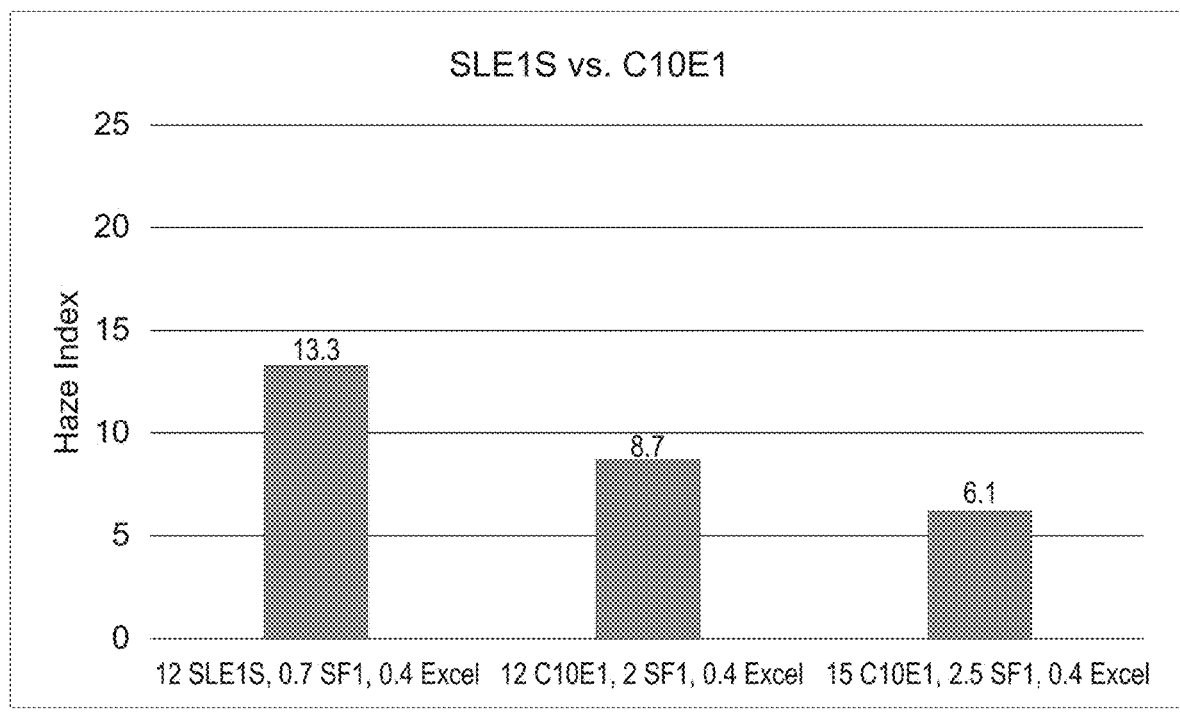
FIG. 12 is a graph demonstrating Sodium Deceth-1 Sulfate (C10E1) surfactant containing formulas are more clear and haze values are lower, verses Sodium Laureth-1 Sulfate (SLE1S) containing formulas.

[1]Sodium Laureth-1 Sulfate at 26% active, supplier: P&G
[2]Sodium Deceth-1 Sulfate at 35% active, supplier P&G
[3]Carbopol Aqua SF1-1 at 30% active, supplier Lubrizol
[4]Octopirox; supplier: Clariant
[5]Jaguar Excel, Solvay Novecare
[6]Dissolvine 220-S at 84% active, supplier: Akzo Nobel
[7]Sodium Benzoate Dense NF/FCC, supplier: Emerald Performance Materials
[8]Sodium Chloride, supplier: Morton; level adjustable to achieve target viscosity
[9]Citric Acid Anhydrous, supplier: Archer Daniels Midland; level adjustable to achieve target pH
[10]Kathon CG at 1.5% active, supplier: Rohm & Haas FIG. 12 data demonstrates that all C10E1 containing formulas are more clear, haze values are lower, verses all SLE1S containing formulas. FIG. 12 data also shows that when the C10E1 level is increased the haze value decreases, meaning the shampoo appearance is clearer with more C10E1.

FIG. 12 demonstrates 12% Sodium Laureth-1 Sulfate (SLE1S) surfactant in combination with 0.7% SF1 and 0.4% Jaguar Excel. FIG. 12 demonstrates 12% Sodium Deceth-1 Sulfate (C10E1) in combination with 2% SF1 and 0.4% Jaguar Excel. Lastly, FIG. 12 demonstrates 15% Sodium Deceth-1 Sulfate (C10E1) in combination with 2.5% SF1 and 0.4% Jaguar Excel.

| Raw Material | Example 30 Target % | Example 27 Target % | Example 28 Target % |
|---|---|---|---|
| SLE1S[1] | 12.00 | 0.00 | 0.00 |
| C10E1[2] | 0.00 | 12.00 | 15.00 |
| Acrylate Copolymer[3] | 0.70 | 2.00 | 2.50 |
| Piroctoneolamille[4] | 0.50 | 0.50 | 0.50 |
| Guar Hydroxypropyltrimonium Chloride[5] | 0.40 | 0.40 | 0.40 |
| CMEA[6] | — | — | — |
| EDTA[7] | 0.13 | 0.13 | 0.13 |
| Sodium Benzoate[8] | 0.15 | 0.15 | 0.15 |
| Sodium Chloride[9] | 1.10 | 1.10 | 0.15 |
| Citric Acid[10] | 0.50 | 0.50 | 0.50 |
| Sodium Salicylate[11] | 0.15 | 0.15 | 0.15 |
| Fragrance | 1.10 | 1.10 | 1.10 |
| Haze Value | 13.3 | 8.7 | 6.1 |
| Viscosity (cps) | 7366 | 6,471 | 7,556 |
| pH | 5.4 | 5.50 | 5.52 |

[1]Sodium Laureth-1 Sulfate at 26% active, supplier: P&G
[2]Sodium Deceth-1 Sulfate at 35% active, supplier P&G
[3]Carbopol Aqua SF1-1 at 30% active, supplier Lubrizol
[4]Octopirox; supplier: Clariant
[5]Jaguar Excel, Solvay Novecare
[6]Cocamide MEA at 10% active, supplier P&G
[7]Dissolvine 220-S at 84% active, supplier: Akzo Nobel
[8]Sodium Benzoate Dense NF/FCC, supplier: Emerald Performance Materials
[9]Sodium Chloride, supplier: Morton; level adjustable to achieve target viscosity
[10]Citric Acid Anhydrous, supplier: Archer Daniels Midland; level adjustable to achieve target pH
[11]Sodium Salicylate, supplier Alta Laboratories The following examples are presented to further illustrate, but not to limit, the present invention

| Raw Material | Example 29 Target % |
|---|---|
| SLE1S[1] | 12.00 |
| C10E1[2] | 5.00 |
| Acrylate Copolymer[3] | 0.70 |
| Piroctoneolamine[4] | 0.50 |
| Guar Hydroxypropyltrimonium Chloride[5] | 0.40 |
| CMEA[6] | 0.25 |
| EDTA[7] | 0.13 |
| Sodium Benzoate[8] | 0.15 |
| Sodium Chloride[9] | 0.00 |
| Citric Acid[10] | 0.46 |
| Sodium Salicylate[11] | 0.15 |
| Fragrance | 1.10 |

[1]Sodium Laureth-1 Sulfate at 26% active supplier: P&G

-continued

| Raw Material | Example 29 Target % |
|---|---|

²Sodium Deceth-1 Sulfate at 35% active, supplier P&G
³Carbopol Aqua SF1-1 at 30% active, supplier Lubrizol
⁴Octopirox; supplier: Clariant
5Jaguar Excel, Solvay Novecare
⁶Cocamide MEA at 10% active, supplier P&G
⁷Dissolvine 220-S at 84% active, supplier: Akzo Nobel
⁸Sodium Benzoate Dense NF/FCC, supplier: Emerald Performance Materials
⁹Sodium Chloride, supplier: Morton; level adjustable to achieve target viscosity
¹⁰Citric Acid Anhydrous, supplier: Archer Daniels Midland; level adjustable to achieve target pH
¹¹Sodium Salicylate, supplier Alta Laboratories The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) from about 12% to about 14% of a combination of surfactants comprising sodium laureth-n sulfate where n is between about 0.5 to about 3.5 and sodium deceth-n sulfate where n is between about 0.5 to about 3.5;
   b) from about 0.5% to 3% of one or more soluble scalp health active wherein the soluble scalp health active comprises piroctone olamine;
   c) from about 0.7% to about 1% of a thickening polymer wherein the thickening polymer comprises an acrylate copolymer;
   d) from 0.1% to 0.4% of a cationic polymer wherein the cationic polymer is selected from the group consisting of a cationic guar polymer, a cationic cellulose polymer or mixtures thereof wherein the cationic polymer has a molecular weight of from about 400,000 g/mol to about 2.0 million g/mol and a charge density of about 0.7 meq/g to about 1.25 meq/g;
   wherein the personal care composition has a pH of about 4.5 to about 6 and wherein the personal care composition has a Haze value less than or equal to 25.

2. A personal care composition according to claim 1 further comprising from about 0.25% to about 15% of one or more amphoteric, nonionic or zwitterionic co-surfactants.

3. A personal care composition according to claim 1 wherein the pH of the composition is from about 5 to about 6.

4. A personal care composition according to claim 1 wherein the personal care composition has a Haze value less than or equal to 10.

5. A personal care composition according to claim 1 wherein the personal care composition has a Haze value less than or equal to 9.

6. A personal care composition according to claim 1 wherein the personal care composition has a Haze value less than or equal to 8.

7. A personal care composition according to claim 1 wherein the personal care composition has a Haze value less than or equal to 7.

8. A personal care composition according to claim 1 wherein the personal care composition has a Haze value less than or equal to 3.

9. A personal care composition according to claim 1 wherein the pH of the composition is from about 4 to about 5.

10. A personal care composition according to claim 1 wherein the composition further comprises a conditioning agent.

11. A personal care composition according to claim 10 wherein the conditioning agent is a silicone.

12. A personal care composition according to claim 11 wherein the silicon has a particle size less than 100 nm.

13. A personal care composition according to claim 1 further comprising one or more scalp health agent.

14. A personal care composition according to claim 13 wherein the one or more scalp health agent is salicylic acid.

15. A personal care composition according to claim 13 wherein the one or more scalp health agent is menthol and/or menthyl lactate.

16. A personal care composition according to claim 1 further comprising from about 0.5% to about 7% of a perfume.

* * * * *